(12) United States Patent
Kuri

(10) Patent No.: US 9,522,538 B2
(45) Date of Patent: Dec. 20, 2016

(54) IMAGE FORMING APPARATUS AND DIRTINESS DETECTION METHOD

(71) Applicant: Seiko Epson Corporation, Tokyo (JP)

(72) Inventor: Ryohei Kuri, Matsumoto (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/061,136

(22) Filed: Mar. 4, 2016

(65) Prior Publication Data

US 2016/0263895 A1 Sep. 15, 2016

(30) Foreign Application Priority Data

Mar. 9, 2015 (JP) .................. 2015-046370

(51) Int. Cl.
*B41J 2/165* (2006.01)
(52) U.S. Cl.
CPC ..................... *B41J 2/165* (2013.01)
(58) Field of Classification Search
CPC ....... B41J 11/006; B41J 11/0075; B41J 11/20; B41J 11/32; B41J 11/42; B41J 11/425; B41J 13/26; B41J 15/046; B41J 15/24; B41J 19/145; B41J 19/147; B41J 2/04503; B41J 2/04505; B41J 2/04506; B41J 2/04508; B41J 2/0451; B41J 2/04513; B41J 2/04515; B41J 2/04518; B41J 2/0452; B41J 2/04521; B41J 2/04525; B41J 2/04526; B41J 2/04535; B41J 2/04536; B41J 2/04538; B41J 2/0454; B41J 2/04545; B41J 2/04551; B41J 2/04553; B41J 2/04555; B41J 2/04556; B41J 2/04558; B41J 2/0456; B41J 2/04561; B41J 2/04565; B41J 2/04566; B41J 2/04568; B41J 2/0457; B41J 2/04571; B41J 2/04573; B41J 2/0459; B41J 2/04591; B41J 2/115; B41J 2/12; B41J 2/125; B41J 2/14153; B41J 2/165; B41J 2/16517; B41J 2/16579; B41J 2/17543; B41J 2/17546; B41J 2/1755; B41J 2/17556; B41J 2/17566; B41J 2/195; B41J 2/20; B41J 2/2132; B41J 2/2135; B41J 2/2139; B41J 2/2142; B41J 2/2146; B41J 2/512; B41J 2002/062; B41J 2002/14354; B41J 2002/1657; B41J 2002/16573; B41J 2002/17569; B41J 2002/17573; B41J 2002/17576; B41J 2002/17579; B41J 2002/17583; B41J 2002/17586; B41J 2002/17589; B41J 2029/3932; B41J 2029/3935; B41J 2029/3937; B41J 2202/07; B41J 2202/08; B41J 2202/17; B41J 2202/18; B41J 25/003; B41J 29/393; B41J 29/42; B41J 29/44; B41J 29/46; B41J 29/48; B41J 29/60; B41J 29/62; B41J 29/66; B41J 29/68

See application file for complete search history.

(56) References Cited

U.S. PATENT DOCUMENTS 7,325,894 B2 * 2/2008 Kodama .................... B41J 2/19
347/7
7,775,624 B2 * 8/2010 Kusakari ................. B41J 2/165
347/19

(Continued)

FOREIGN PATENT DOCUMENTS

GB 2472857 A 2/2011
JP 11-142752 A 5/1999

(Continued)

OTHER PUBLICATIONS

Extended European Search Report for EP Application No. 16158908.0, dated Jul. 21, 2016 (7 pages).

*Primary Examiner* — Kristal Feggins
(74) *Attorney, Agent, or Firm* — Harness, Dickey & Pierce, P.L.C.

(57) ABSTRACT

A printer includes a printing section that ejects an ink, and a spectrometer that disperses incident light. The spectrom- (Continued)

eter includes a window section that transmits the light, an optical filter device, and a light receiving section. The optical filter device includes a variable wavelength interference filter as a dispersing element that disperses light transmitted by the window section. The light receiving section receives the light which is dispersed by the variable wavelength interference filter. A dirtiness of the window section is detected based on measured values corresponding to each of a plurality of wavelengths obtained by spectrally measuring light from a reference object, and reference values corresponding to each of the plurality of wavelengths.

13 Claims, 14 Drawing Sheets

(56) References Cited

U.S. PATENT DOCUMENTS

| 8,757,767 B2 * | 6/2014 | Inoue | B41J 2/16535 347/31 |
|---|---|---|---|
| 2004/0005469 A1 | 1/2004 | Metz et al. | |
| 2009/0229067 A1 | 9/2009 | Becker et al. | |
| 2014/0050496 A1 | 2/2014 | Furuta | |
| 2014/0199085 A1 | 7/2014 | Matsui et al. | |

FOREIGN PATENT DOCUMENTS

| JP | 2013-217654 A | 10/2013 |
|---|---|---|
| JP | 2014-137459 A | 7/2014 |
| WO | WO-2008-087648 A2 | 7/2008 |

* cited by examiner

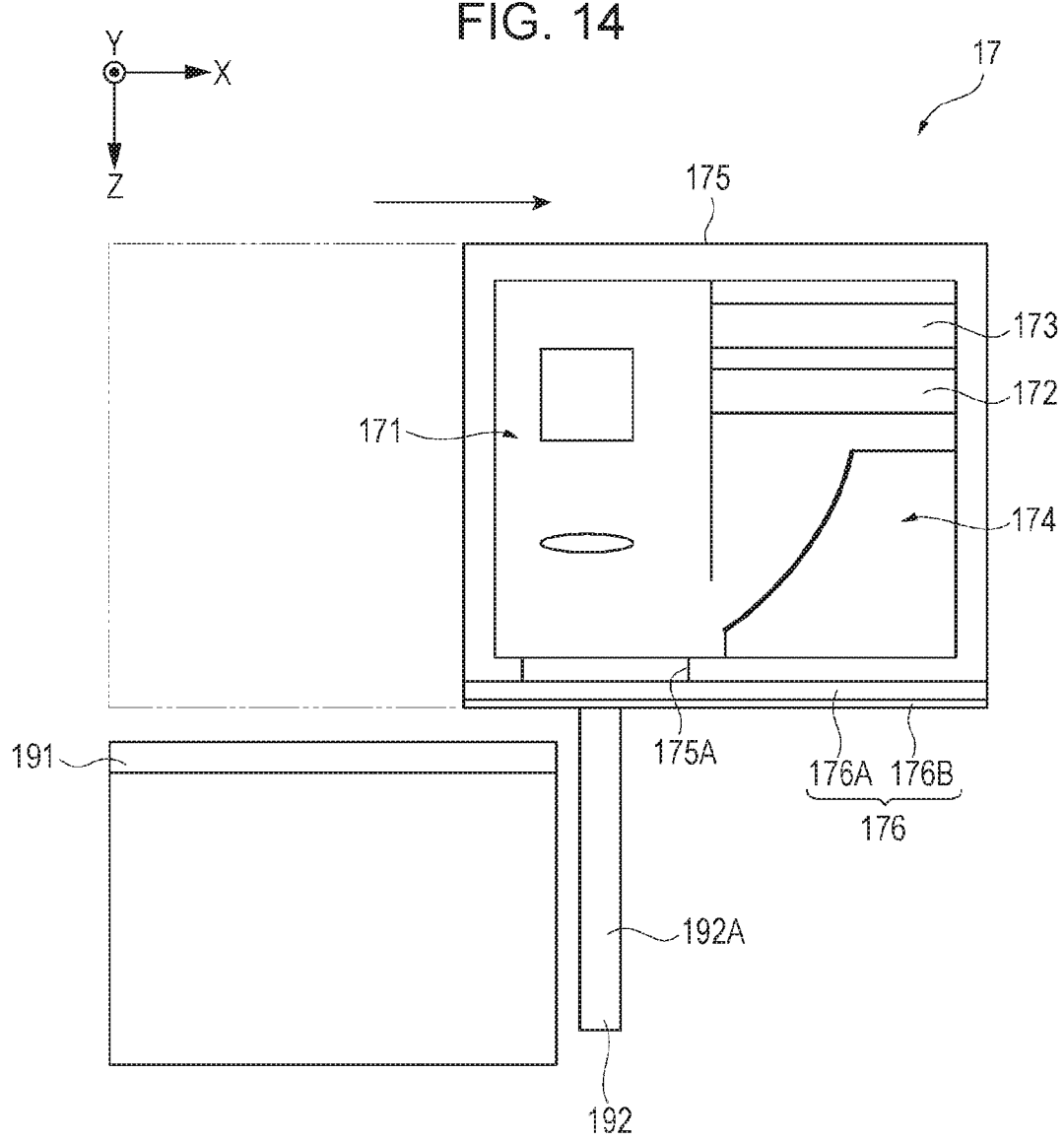

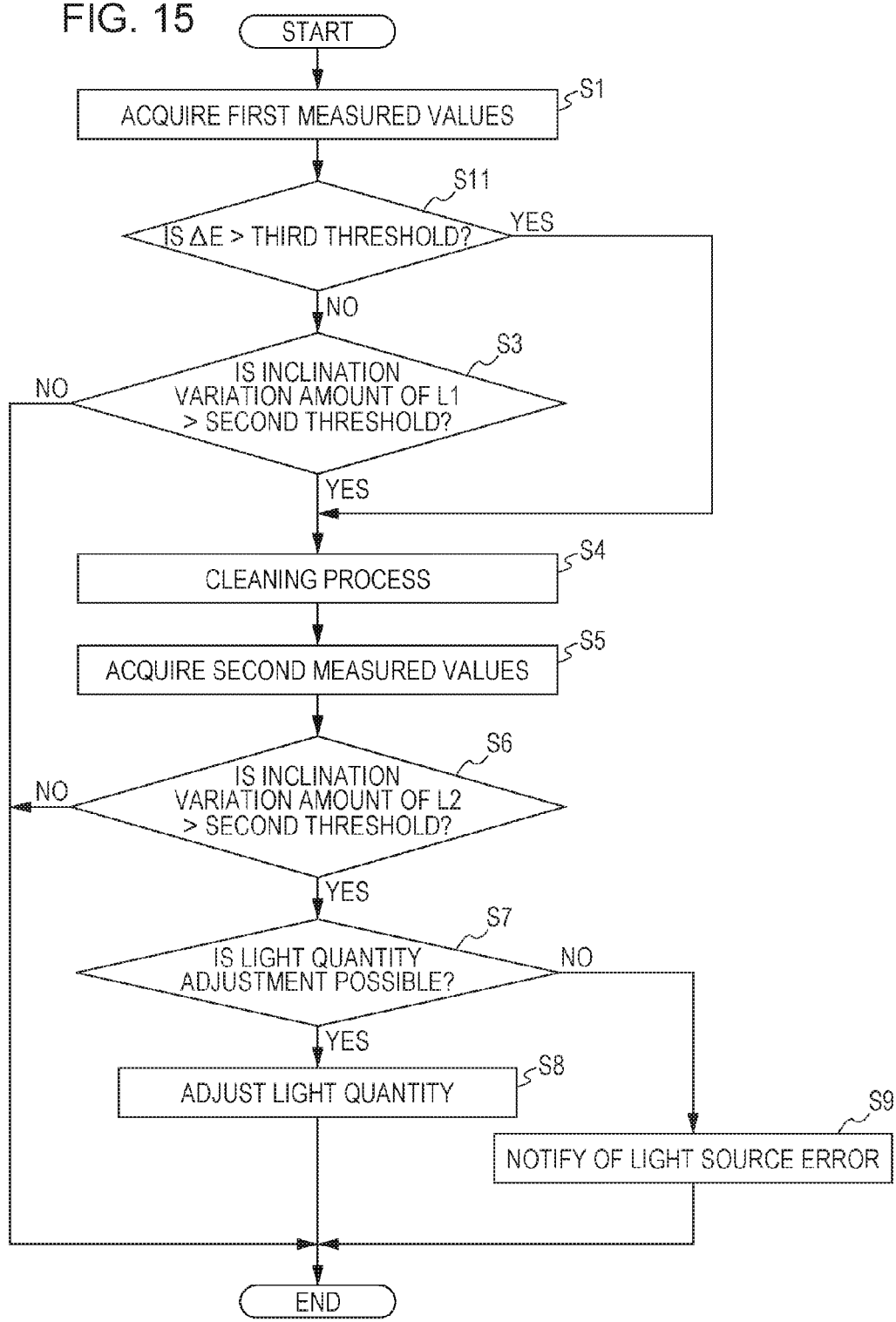

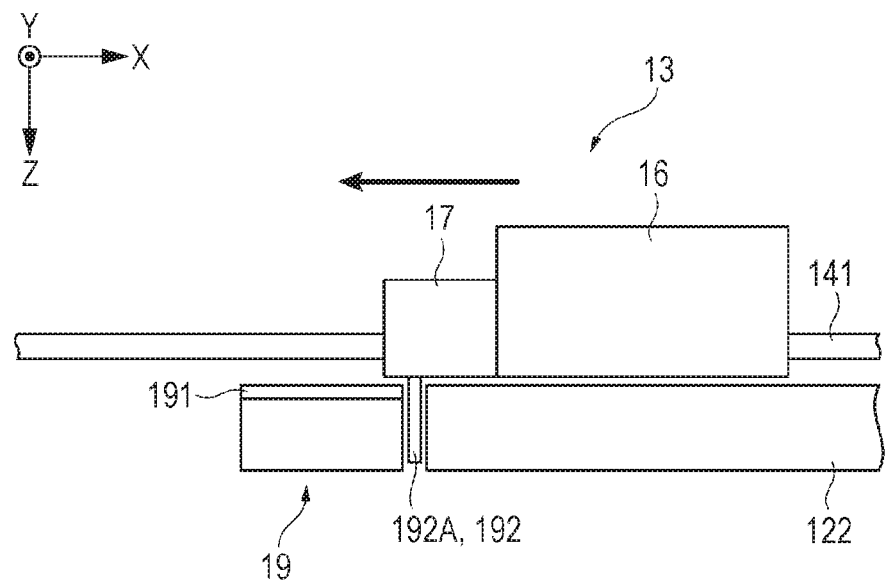
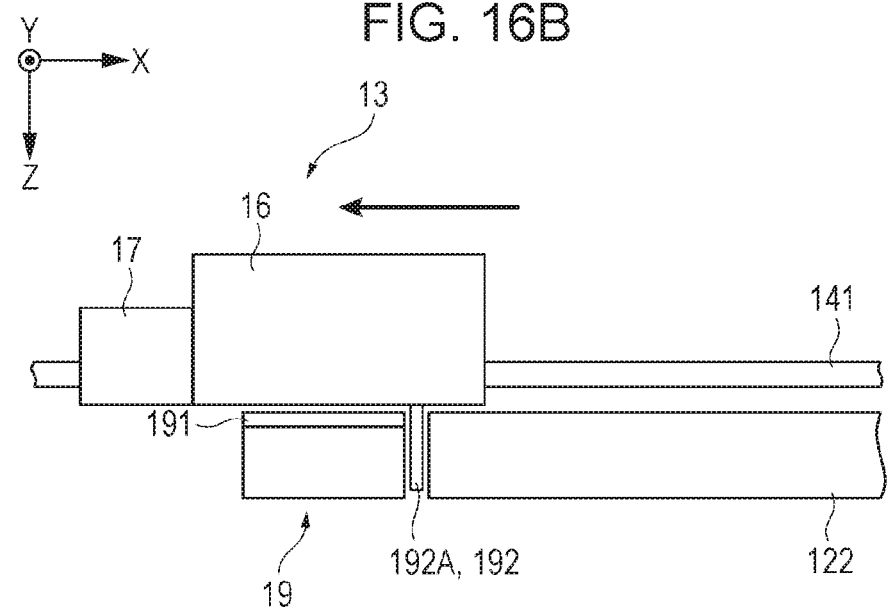

IMAGE FORMING APPARATUS AND DIRTINESS DETECTION METHOD

BACKGROUND

1. Technical Field

The present disclosure relates to an image forming apparatus and a dirtiness detection method.

2. Related Art

In the related art, there is known a recording apparatus provided with a recording head having an ink jet recording system and a color measurement unit. The ink jet recording system records an image by ejecting ink onto a recording medium. The color measurement unit performs color measurement of the image which is recorded on the recording medium. See, for example, JP-A-2013-217654.

In the recording apparatus described in JP-A-2013-217654, a color measurement unit is provided with a color measurement carriage capable of moving along a recording medium. A color measurement sensor is disposed inside the color measurement carriage. The color measurement unit is configured to be capable of moving the color measurement carriage to the recording medium and carrying out color measurement using the color measurement sensor.

Incidentally, in the apparatus described in JP-A-2013-217654, since the ink jet recording system is adopted, there is a case in which an ink mist is generated when the ink is ejected from the recording head, and the ink adheres to the color measurement sensor. Here, when the ink adheres to an element on the optical path of the light of the color measurement target of the color measurement sensor, light of a wavelength corresponding to the color of the adhered ink is absorbed from the light of the color measurement target. Therefore, the color measurement precision may be reduced.

However, in the related art, there is a problem in that a reduction in the color measurement precision due to dirt (e.g., ink residue) on the color measurement sensor caused by the adherence of ink or the like may not be detected.

SUMMARY

An advantage of some aspects of the invention is to provide an image forming apparatus and a dirtiness detection method which are capable of detecting a reduction in color measurement precision due to dirtiness.

According to an application example of the invention, there is provided an image forming apparatus which includes an image forming unit that ejects an ink, and a spectrometer that disperses incident light. The spectrometer includes a window section that transmits the light, a dispersing element that disperses light transmitted by the window section, and a light receiving element that receives the light which is dispersed by the dispersing element. Dirt (i.e., a residue) on the window section is detected based on measured values corresponding to each of a plurality of wavelengths obtained by spectrally measuring light from a reference object, and reference values corresponding to each of the plurality of wavelengths.

Examples of measured values include the light reception signal which is output from the light receiving element in relation to each of the plurality of wavelengths, the light quantity values which are calculated from the light reception signal, and the reflectance which is calculated based on the light quantity values.

For example, the measured values of the reference object in a state in which the window section is not dirtied (e.g., does not have a residue of ink) are used as the reference values. In other words, it is possible to use the measured values (the initial values) which are measured in advance during manufacture, measured values which are acquired directly after carrying out the cleaning of the window section, and the like, as the reference values.

The image forming apparatus according to the application example may further include a spectral measurement unit that acquires the measured values, and a dirtiness detecting unit that detects dirtiness of the window section.

In this application example, the measured values are acquired by carrying out the spectral measurement of the reference object, and the dirtiness of the window section is detected based on the reference values and the measured values.

Here, the light from the reference object is incident on the dispersing element via the window section. Therefore, when the ink, which is ejected from the image forming section, adheres to the window section, since light of a specific wavelength corresponding to the color of the ink adhered to the window section is absorbed when the light from the reference object passes through the window section, the measured values change. Therefore, it is possible to detect the ink residue on the window section by detecting the variation in the measured values caused by the ink based on the reference values (for example, the measured values which are a reference of a case in which the window section is not dirtied) and the measured values, and it is possible to detect a reduction in the color measurement precision caused by the ink dirtiness.

In the image forming apparatus according to the application example, it is preferable that the dirtiness detecting unit detects dirtiness of the window section based on a correlation between the reference values and the measured values.

Note that, in this application example, performing the detection based on a correlation coefficient, for example, is exemplified as the method of detecting the dirtiness of the window section based on the correlation between the reference values and the measured values. More specifically, detecting the dirtiness when the magnitude of the correlation coefficient is less than a threshold is exemplified. As the threshold in this case, for example, a threshold of the magnitude of the correlation coefficient of a case in which the color difference based on the reference values and the measured values in relation to the color measurement precision is small and can be treated as substantially the same color may be used.

In this application example, the measured values are acquired by carrying out the spectral measurement of the reference object in relation to a plurality of wavelengths, and the dirtiness of the window section is detected based on the correlation between the reference values and the measured values.

Here, as described above, when the ink adheres to the window section, since light of a specific wavelength corresponding to the color of the ink is absorbed when the light from the reference object passes through the window section, the measured values change. Therefore, the correlation between the reference values and the measured values is changed in comparison to when the window section is not dirtied with ink. More specifically, since the measured values also change due to a reduction in the light quantity at a specific wavelength in comparison to when there is no ink dirtiness (i.e., ink residue), the magnitude of the correlation coefficient decreases.

In this manner, in this application example, it is possible to detect the ink dirtiness of the window section based on the correlation based on the reference values and the measured values, and it is possible to detect a reduction in the color measurement precision caused by the ink dirtiness.

In the image forming apparatus according to the application example, the dirtiness detecting unit may detect dirtiness of the window section based on a color variation between the reference values and the measured values.

Note that, in an example of the method of detecting the dirtiness of the window section based on the color variation between the reference values and the measured values, the reference values and the measured values are used to calculate the color difference, the variation in the chromaticity (variation in the hue or the chroma) or the like as the evaluation values with which to quantitatively evaluate the color variation. The color variation is determined based on the evaluation values, and the dirtiness of the window section is detected.

In this application example, the dirtiness of the window section is detected based on the color variation between the reference values and the measured values.

Here, when the ink adheres to the window section, since light of a specific wavelength corresponding to the color of the ink which is adhered to the window section is absorbed, the color varies between the reference values and the measured values. In this application example, by detecting the color variation based on the reference values and the measured values, it is possible to detect that ink is adhered to the window section, and it is possible to detect a reduction in the color measurement precision caused by the adherence of the ink.

The image forming apparatus according to the application example further includes a cleaning mechanism which cleans the window section, and a cleaning control unit which causes the cleaning mechanism to carry out the cleaning of the window section when dirt is detected by the dirtiness detecting unit.

In this application example, when dirtiness of the window section is detected, the cleaning is carried out using the cleaning mechanism. Accordingly, it is possible to remove the ink which is adhered to the window section, and it is possible to suppress a reduction in the color measurement precision caused by the adherence of the ink.

In the image forming apparatus according to the application example, the cleaning mechanism may include an abutting member which abuts the window section when the cleaning of the window section is carried out and is positioned in a standby position distanced from the window section at times other than when the cleaning is carried out.

In this application example, in the cleaning mechanism, at times other than during the cleaning, the abutting member is disposed in a standby position. Accordingly, it is possible to suppress the wearing (the degradation) of the abutting member caused by the abutting member abutting the window section at times other than during the cleaning, and it is possible to maintain the cleaning performance.

The image forming apparatus according to the application example further includes a light quantity variation determination unit which determines whether or not there is variation in a light quantity of a light source based on a slope of a regression line. The regression line may be based on the reference values and the measured values. The spectrometer includes the light source which irradiates a target with light via the window section.

In this application example, the light quantity variation determination unit acquires the regression line based on the reference values and the measured values and determines whether or not there is variation in the light quantity of the light source based on the slope of the regression line.

Here, the measured values are values corresponding to the light quantity received by the light receiving element, and the measured values vary according to the light quantity of the light source. Therefore, when there is no variation in the slope of the regression line based on the measured values, it is possible to determine that there is no variation in the light quantity of the light source, and when there is variation in the slope, it is possible to determine that there is a likelihood that there is variation in the light quantity of the light source. In this manner, in this application example, it is possible to determine whether or not there is variation in the light quantity of the light source by referring to the slope of the regression line.

In the image forming apparatus according to the application example, the light quantity variation determination unit determines that there is variation in the light quantity of the light source when the slope falls outside of a predetermined allowable range.

Note that, the predetermined allowable range of the slope may be an allowable range of the slope of the regression line corresponding to the allowable range of the variation in the light quantity of the light source. If the slope of the regression line falls within the predetermined allowable range, the variation in the light quantity of the light source is also allowed.

Ordinarily, when the light quantity is reduced due to degradation or the like of the light source, the greater the light quantity of a wavelength, the greater the variation amount of the light quantity, and the smaller the light quantity of a wavelength, the smaller the variation amount of the light quantity.

Here, when the same type of values such as the light quantity values are used for both the reference values which are the predictor variable and the measured values which are the criterion variable, the slope of the regression line decreases in relation to 1 corresponding to a decrease in the measured values in relation to the reference values. In this manner, the variation in the slope of the regression line corresponds to variation in the light quantity of the light source. Therefore, it is possible to determine whether or not the light quantity of the light source varies in excess of the allowable range based on whether or not the slope of the regression line falls within the allowable range.

The image forming apparatus according to the application example may further include a light quantity variation determination unit which determines whether or not there is variation in a light quantity of a light source based on a slope of a regression line based on the reference values and the measured values, in which the spectrometer includes the light source which irradiates a target with light via the window section, and in which after the cleaning of the window section is carried out, the light quantity variation determination unit determines whether or not there is variation in the light quantity of the light source based on a slope of a regression line based on the measured values and the reference values.

Here, the measured values are values corresponding to the light quantity received by the light receiving element, and the measured values vary according to variation in the light quantity of the light source, dirtiness of the window section, and the like. Therefore, when the slope of the regression line changes, other than the influence of the variation in the light quantity of the light source, there is a likelihood that the change is caused by the influence of a reduction in the received light quantity caused by the dirtiness of the window section.

To handle this, since the slope of the regression line is referred to after the cleaning is carried out, it is possible to suppress the influence of the dirtiness of the window section, and it is possible to more reliably determine whether or not there is variation in the light quantity of the light source.

In the image forming apparatus according to the application example, the window section includes a light transmissive member and a hydrophobic film which is formed on a surface of the target side of the light transmissive member.

According to this application example, it is possible to easily remove the ink even when the ink is adhered to the window section due to the surface of the light transmissive member being covered with a hydrophobic material. Therefore, it is possible to improve the maintainability.

In the image forming apparatus according to the application example, the dispersing element may be a variable-wavelength type Fabry-Pérot etalon.

In this application example, the variable-wavelength type Fabry-Pérot etalon is used as a dispersing element. Accordingly, by sequentially changing the dimension of the space between the pair of reflecting surfaces, it is possible to extract light of a plurality of wavelengths in a short time, and it is possible to obtain a shortening in the time necessary for measurement. By using the Fabry-Pérot etalon which has a small size, it is possible to obtain a reduction in the size of the image forming apparatus in comparison to a case in which an acousto-optic tunable filter (AOTF), a liquid crystal tunable filter (LCTF) or the like is used.

According to another application example, there is provided a dirtiness detection method which includes acquiring measured values corresponding to each of a plurality of wavelengths by spectrally measuring light from a reference object, and detecting dirtiness of a window section which transmits light from the reference object based on the measured values and reference values corresponding to each of the plurality of wavelengths.

In this application example, it is possible to obtain the same effects as the image forming apparatus of the application example described above.

BRIEF DESCRIPTION OF THE DRAWINGS

The disclosure will be described with reference to the accompanying drawings, wherein like numbers reference like elements.

FIG. 14 is a schematic diagram illustrating an example of a procedure of the cleaning in the first embodiment.

FIG. 15 is a flowchart illustrating an adjustment process in a printer of a second embodiment.

FIGS. 16A and 16B are schematic diagrams illustrating procedures of cleaning in a modification example according to the disclosure.

DESCRIPTION OF EXEMPLARY EMBODIMENTS

First Embodiment

Hereinafter, description will be given of the first embodiment according to the disclosure based on the drawings. In the present embodiment, hereinafter, description will be given of a printer 10 (an ink jet printer) which is an example of the image forming apparatus of the disclosure.

Schematic Configuration of Printer

Figure 1:
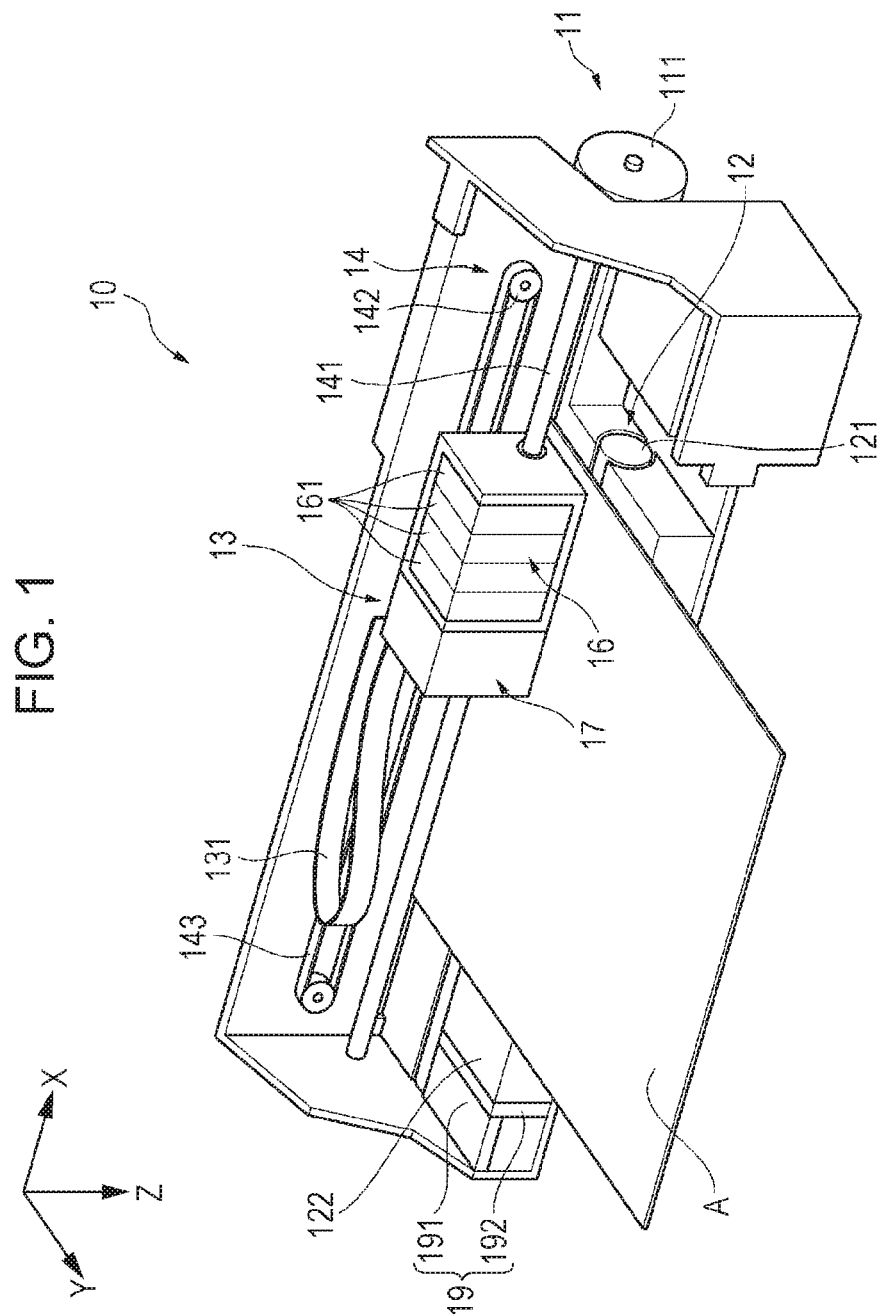
FIG. 1 is a schematic configuration of a printer of a first embodiment according to the disclosure.
Figure 2:
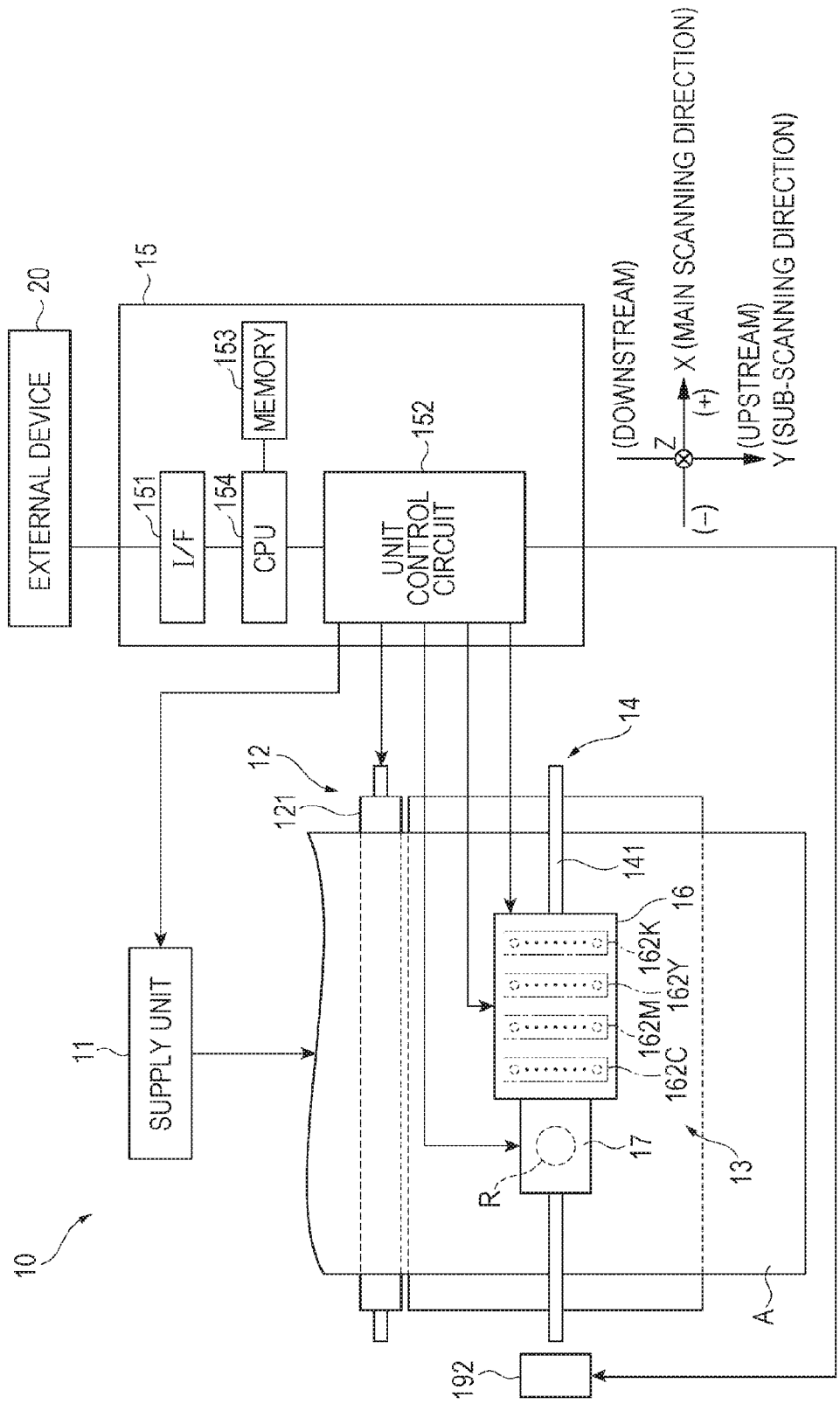
FIG. 2 is a block diagram illustrating the schematic configuration of the printer of the first embodiment.

FIG. 1 is a diagram illustrating a configuration example of the appearance of the printer 10 of the first embodiment. FIG. 2 is a block diagram illustrating the schematic configuration of the printer 10 of the present embodiment.

As illustrated in FIG. 1, the printer 10 is provided with a supply unit 11, a transport unit 12, a carriage 13, a carriage movement unit 14, a control unit 15 (refer to FIG. 2), and an adjustment unit 19. The printer controls each of the units 11, 12, and 14, and the carriage 13 based on print data which is input from an external device 20, such as a personal computer, and prints an image onto a medium A. The printer 10 of the present embodiment detects dirtiness of a window section 176 (refer to FIG. 3) of a spectrometer 17 provided on the carriage 13, and carries out the cleaning of the window section 176 using a cleaning mechanism 192 of the adjustment unit 19.

Hereinafter, specific description will be given of the configuration of the printer 10.

Configuration of Supply Unit

The supply unit 11 supplies the medium A, such as a white paper surface in the present embodiment, which is an image formation target to an image formation position. For example, the supply unit 11 is provided with a roll body 111 (refer to FIG. 1), a roll drive motor (not shown), and a roll drive wheel train (not shown). The medium A is wound on the roll body 111. The roll drive motor is rotationally driven based on the commands from the control unit 15, and the rotational force of the roll drive motor is transmitted to the roll body 111 via the roll drive wheel train. Accordingly, the roll body 111 rotates and the paper surface, which is wound on the roll body 111, is supplied to the downstream side (the +Y direction) in the Y direction (the sub-scanning direction).

Note that, in the present embodiment, an example given in which the paper surface, which is wound on the roll body 111, is supplied; however, the disclosure is not limited thereto. For example, the medium A may be supplied using any supply method, such as supplying the medium A, such as a paper surface stacked on a tray or the like, one sheet at a time using a roller or the like.

Configuration of Transport Unit

The transport unit 12 transports the medium A which is supplied from the supply unit 11 along the Y direction. In other words, the transport unit 12 is a sub-scan moving unit which causes the carriage 13 to move relative to the medium A in the sub-scanning direction. The transport unit 12 is configured to include a transport roller 121, a driven roller (not shown), and a platen 122. The driven roller is disposed to pinch the medium A between the transport roller 121 and itself and is driven by the transport roller 121.

When the drive force from the transport motor (not shown) is transmitted to the transport roller 121 and the transport motor is driven under the control of the control unit 15, the transport roller 121 is rotationally driven by the rotational force and transports the medium A along the Y direction in a state in which the medium A is interposed between the transport roller 121 and the driven roller. The platen 122 facing the carriage 13 is provided on the downstream side (the +Y side) of the transport roller 121 in the Y direction.

Configuration of Carriage

The carriage 13 is provided with a printing section 16 and the spectrometer 17. The printing section 16 prints an image onto the medium A, and the spectrometer 17 performs spectral measurement of a predetermined measurement target region R (refer to FIG. 2) on the medium A.

The carriage 13 is capable of moving along the main scanning direction (the X direction), which intersects the Y direction due to the carriage movement unit 14.

The carriage 13 is connected to the control unit 15 via a flexible circuit 131 and carries out the printing process (the image forming process in relation to the medium A) of the printing section 16 and the spectral measurement process of the spectrometer 17 based on the commands from the control unit 15.

Note that, detailed description of the configuration of the carriage 13 will be given later.

Configuration of Carriage Movement Unit

The carriage movement unit 14 moves the carriage 13 reciprocally along the X direction (the main scanning direction) based on the commands from the control unit 15. In other words, the carriage movement unit 14 is a main-scan moving unit which causes the carriage 13 to move relative to the medium A in the main scanning direction.

For example, the carriage movement unit 14 is configured to include a carriage guide shaft 141, a carriage motor 142, and a timing belt 143.

The carriage guide shaft 141 is disposed along the X direction and both end portions are fixed to the housing, for example, of the printer 10. The carriage motor 142 drives the timing belt 143. The timing belt 143 is supported to be substantially parallel to the carriage guide shaft 141, and a portion of the carriage 13 is fixed thereto. When the carriage motor 142 is driven based on the commands of the control unit 15, the timing belt 143 travels forward or backward, and the carriage 13, which is fixed to the timing belt 143, is guided by the carriage guide shaft 141 to move reciprocally.

Detailed Configuration of Carriage

Next, description will be given of the configuration of the printing section 16 and the spectrometer 17 which are provided on the carriage 13 based on the drawings.

Configuration of Printing Section

The printing section 16 corresponds to an image forming section of the disclosure and forms an image on the medium A by ejecting inks individually onto the medium A in a portion facing the medium A.

In the printing section 16, ink cartridges 161 corresponding to a plurality of colors of ink are mounted in a detachable manner, and inks are supplied from each of the ink cartridges 161 to ink tanks (not shown) via tubes (not shown). With reference to FIG. 2, a nozzle row (162C, 162M, 162Y, and 162K) including a plurality of nozzles which eject ink droplets and correspond to each color of cyan C, magenta M, yellow Y, and black K, is provided on the bottom surface (a position facing the medium A) of the printing section 16. Piezo elements, for example, are disposed in the nozzles, and, by driving the piezo elements, ink droplets supplied from the ink tank are ejected, land on the medium A, and dots are formed.

Configuration of Spectrometer

Figure 3:
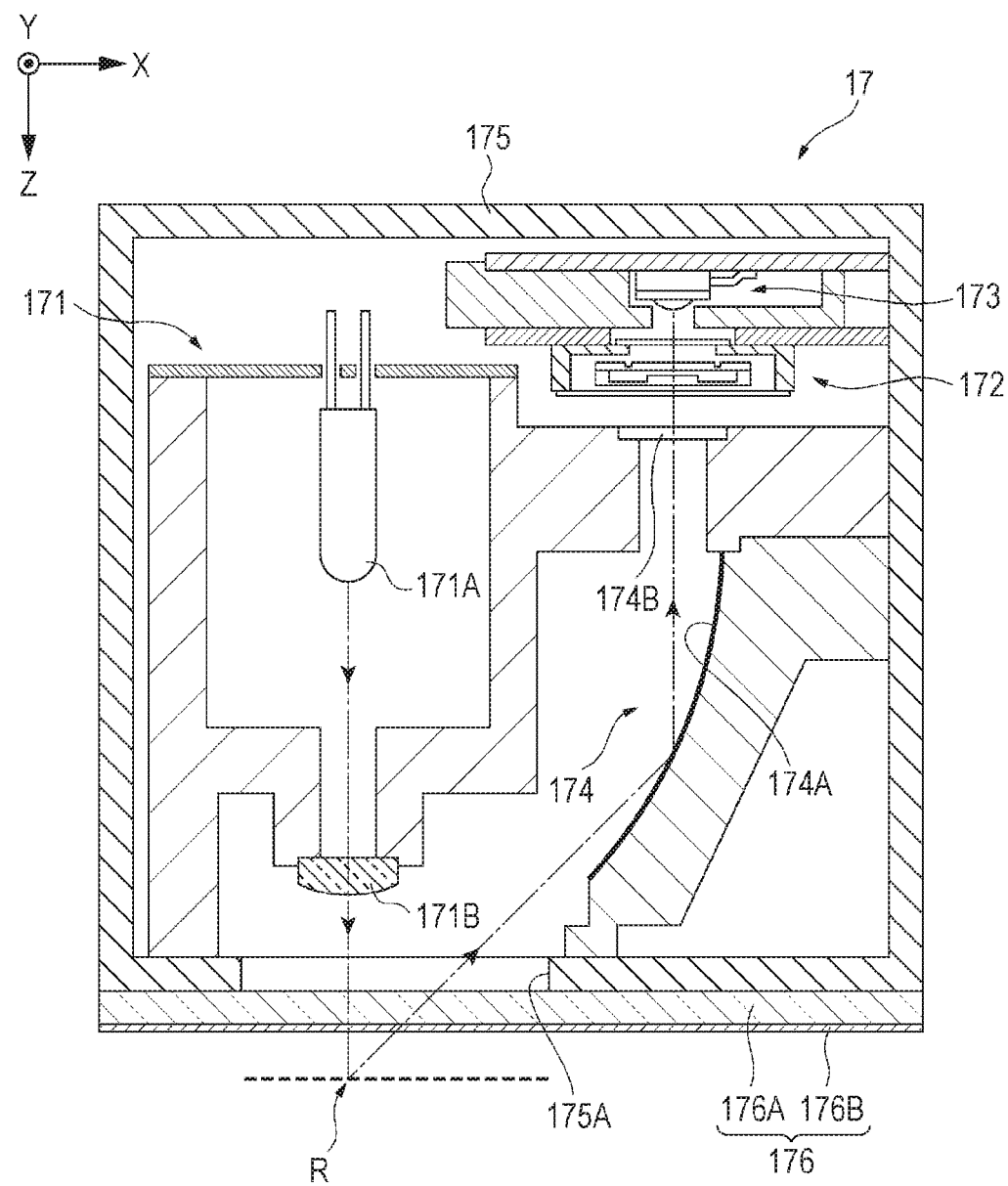
FIG. 3 is a sectional diagram illustrating the schematic configuration of a spectrometer of the first embodiment.

FIG. 3 is a sectional diagram illustrating the schematic configuration of the spectrometer 17.

As illustrated in FIG. 3, the spectrometer 17 is provided with a light source section 171, an optical filter device 172, a light receiving section 173, a light guide section 174, and a spectrometer housing 175. The light receiving section 173 serves as a light receiving element, and the spectrometer housing 175 stores the members 171 to 174 therein.

In the spectrometer 17, the medium A is irradiated with irradiation light from the light source section 171, and the light which is reflected by the medium A is caused to be incident on the optical filter device 172 by the light guide section 174. Light of a predetermined wavelength included in the light reflected by the medium A is allowed to be transmitted (emitted) by the optical filter device 172, and is received by the light receiving section 173. The optical filter device 172 is capable of selecting the wavelength to transmit based on the control of the control unit 15, and it is possible to spectrally measure the measurement target region R on the medium A by measuring the light quantity of the light of each wavelength in visible light.

Configuration of Light Source Section

The light source section 171 is provided with a light source 171A and a condenser section 171B. The light source section 171 irradiates the measurement target region R of the medium A from the normal direction in relation to the surface of the medium A with the light emitted from the light source 171A.

A light source capable of emitting light of each wavelength in the visible light region is preferable as the light source 171A. For example, it is possible to exemplify a halogen lamp, a xenon lamp, or a white LED as the light source 171A, and, in particular, a white LED which can be easily installed within the limited space within the carriage 13 is preferable. The condenser section 171B is formed of a condenser lens, for example, and concentrates the light from the light source 171A on the measurement target region R. Note that, in FIG. 3, only one lens (the condenser lens) is displayed in the condenser section 171B; however, the condenser section 171B may be configured by combining a plurality of lenses.

Configuration of Optical Filter Device

Figure 4:
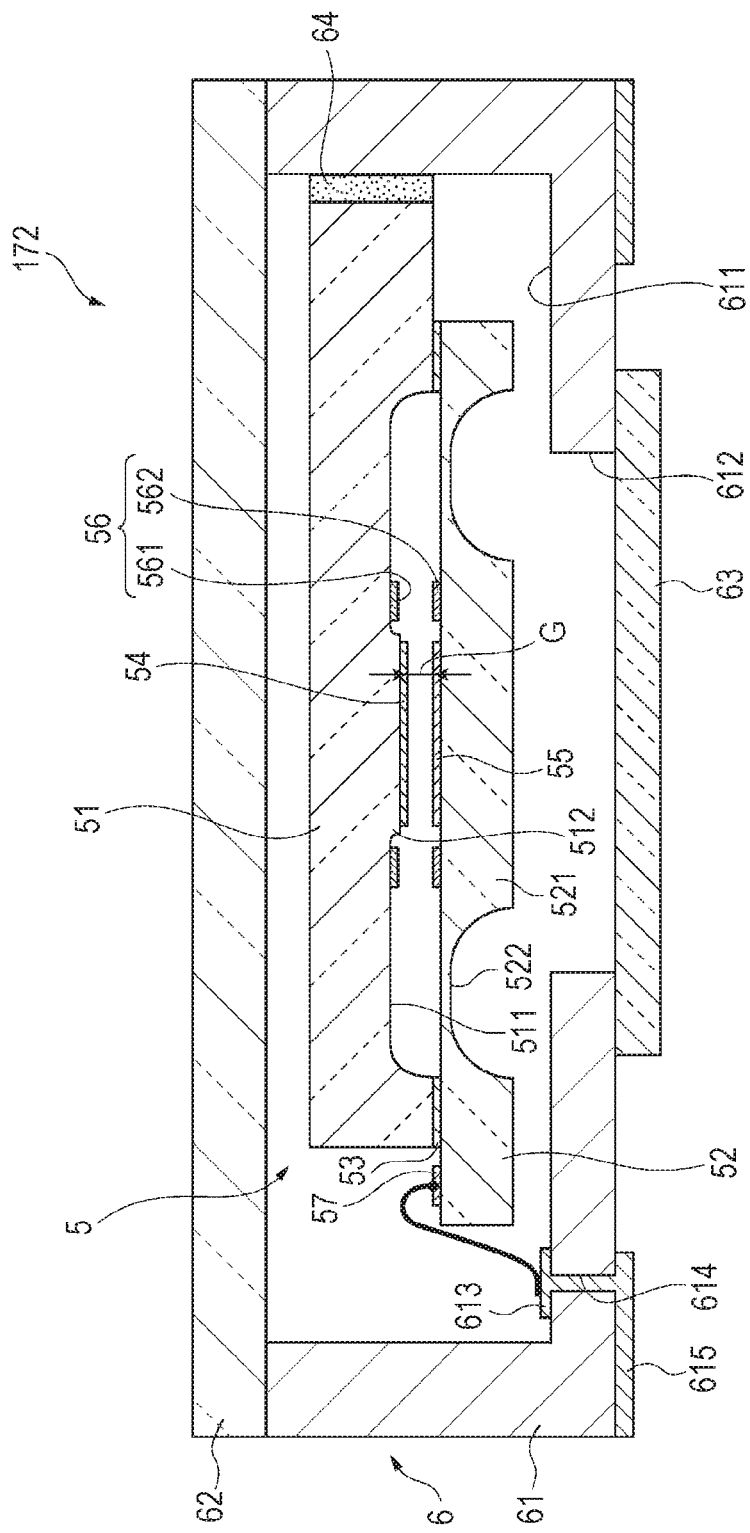
FIG. 4 is a sectional diagram illustrating the schematic configuration of an optical filter device of the first embodiment.

FIG. 4 is a sectional diagram illustrating the schematic configuration of the optical filter device 172.

The optical filter device 172 is provided with a housing 6 and a variable wavelength interference filter 5 which is stored on the inner portion of the housing 6.

Configuration of Variable Wavelength Interference Filter

The variable wavelength interference filter 5 is a variable wavelength type Fabry-Pérot etalon device. As illustrated in FIG. 4, the variable wavelength interference filter 5 is provided with a fixed substrate 51 and a movable substrate 52, which are light transmissive and configured integrally by being bonded by a bonding film 53.

The fixed substrate 51 is provided with a first groove portion 511 and a second groove portion 512 which is shallower than the first groove portion 511. The groove portions 511 and 512 are formed by etching. A fixed electrode 561 is provided in the first groove portion 511, and a fixed reflecting film 54 is provided in the second groove portion 512.

The fixed reflecting film 54 is formed of, for example, a dielectric multilayer film in which high refraction layers and low refraction layers of metal films such as Ag and alloy films such as Ag alloys are laminated, or, is formed of a laminate in which metal films (alloy films) and dielectric films are laminated.

The movable substrate 52 is provided with a movable portion 521 and a holding portion 522. The holding portion 522 is provided on the outside of the movable portion 521 and holds the movable portion 521. A movable electrode 562 facing the fixed electrode 561 and a movable reflecting film facing the fixed reflecting film 54 are provided on a surface of the movable portion 521 facing the fixed substrate 51. A reflecting film of a similar configuration to the fixed reflecting film 54 described above is used as the movable reflecting film 55. The holding portion 522 is a diaphragm surrounding the periphery of the movable portion 521 and is formed to be smaller in the thickness dimension than the movable portion 521.

In the variable wavelength interference filter 5, such as that described above, an electrostatic actuator 56 is formed of the fixed electrode 561 and the movable electrode 562, and by applying a voltage to the electrostatic actuator 56, it becomes possible to change the interval dimension of a gap G between the fixed reflecting film 54 and the movable reflecting film 55. A plurality of electrode pads 57, which are individually connected to the fixed electrode 561 and the movable electrode 562, are provided on the outer circumferential portion (a region not facing the fixed substrate 51) of the movable substrate 52.

Configuration of Housing

As illustrated in FIG. 4, the housing 6 is provided with a base 61 and a glass substrate 62. Due to the base 61 and the glass substrate 62 being bonded by low melting point glass bonding or the like, for example, a storage space is formed on the inner portion thereof, and the variable wavelength interference filter 5 is stored in this storage space.

The base 61 is formed by laminating ceramic onto a thin substrate, for example, and includes a recess portion 611 capable of storing the variable wavelength interference filter 5. The variable wavelength interference filter 5 is fixed to the side surfaces of the recess portion 611 of the base 61 using a fixing material 64. A light-transmitting through hole 612 is provided in the bottom surface of the recess portion 611 of the base 61, and a cover glass 63 which covers the light-transmitting through hole 612 is bonded to the bottom surface.

An inside terminal section 613 which is connected to the electrode pads 57 of the variable wavelength interference filter 5 is provided on the base 61. The inside terminal section 613 is connected to an outside terminal section 615 which is provided on the outside of the base 61 via a conducting hole 614. The outside terminal section 615 is electrically connected to the control unit 15.

Configuration of Light Receiving Section and Light Guide Optical System

Returning to FIG. 3, the light receiving section 173 is disposed over the optical axis of the variable wavelength interference filter 5 and receives the light which is transmitted by the variable wavelength interference filter 5. The light receiving section 173 outputs a detection signal (a current value) according to the received light quantity based on the control of the control unit 15. Note that, the detection signal which is output by the light receiving section 173 is input to the control unit 15 via an I-V converter (not shown), an amplifier (not shown), and an AD converter (not shown).

The light guide section 174 is provided with a reflecting mirror 174A and a band pass filter 174B.

The light guide section 174 reflects the light which is reflected by 45° in relation to the surface of the measurement target onto the optical axis of the variable wavelength interference filter 5 using the reflecting mirror 174A. The band pass filter 174B transmits light in the visible regions (for example, 380 nm to 720 nm) and cuts ultraviolet and infrared light. Accordingly, light in the visible regions is incident on the variable wavelength interference filter 5, and the light of a wavelength selected by the variable wavelength interference filter 5 in the visible regions is received in the light receiving section 173.

Configuration of Spectrometer Housing

The spectrometer housing 175 is a housing which forms the outer casing of the spectrometer 17. As illustrated in FIG. 3, the spectrometer housing 175 includes an opening portion 175A, and is provided with the window section 176 which covers the opening portion 175A.

The opening portion 175A is provided in the surface of the side of the spectrometer housing 175 facing the medium A, and the opening size is set such that the optical path of the light which is emitted from the light source section 171 and the optical path of the light which is reflected from the medium A and incident on the light receiving section 173 are formed on the inside and outside of the spectrometer housing 175. Note that, in the present embodiment, a configuration is adopted in which the optical path of the light which is emitted from the light source section 171 and the optical path of the light which is incident on the light receiving section 173 are included in the single opening portion 175A; however, a configuration may be adopted in which an opening portion which transmits the light from the light source section 171 and an opening portion which transmits the light incident on the light receiving section 173 are provided separately.

The window section 176 includes a member in a position which covers at least the opening portion 175A.

In the present embodiment, the window section 176 is configured to include a light transmissive member 176A and a hydrophobic film 176B which cover the opening portion 175A. The light which is emitted from the light source section 171 is emitted to the outside via the window section 176. The light from the color measurement target (for example, the medium A or a white reference plate 191 described later) enters the inner portion of the spectrometer housing 175 via the window section 176.

The light transmissive member 176A is formed of a light transmissive material having light transmittance in relation to a wavelength region (in the present embodiment, a visible light region) which is measured by the spectrometer 17, and the light transmissive member 176A is disposed to cover the opening portion 175A.

The hydrophobic film 176B is formed on the surface (the surface of the medium A side) of the light transmissive member 176A. The hydrophobic film 176B is formed using a fluorine-based hydrophobic material, for example. Accordingly, it is possible to easily remove ink which is adhered to the window section 176.

Configuration of Adjustment Unit

Figure 5:
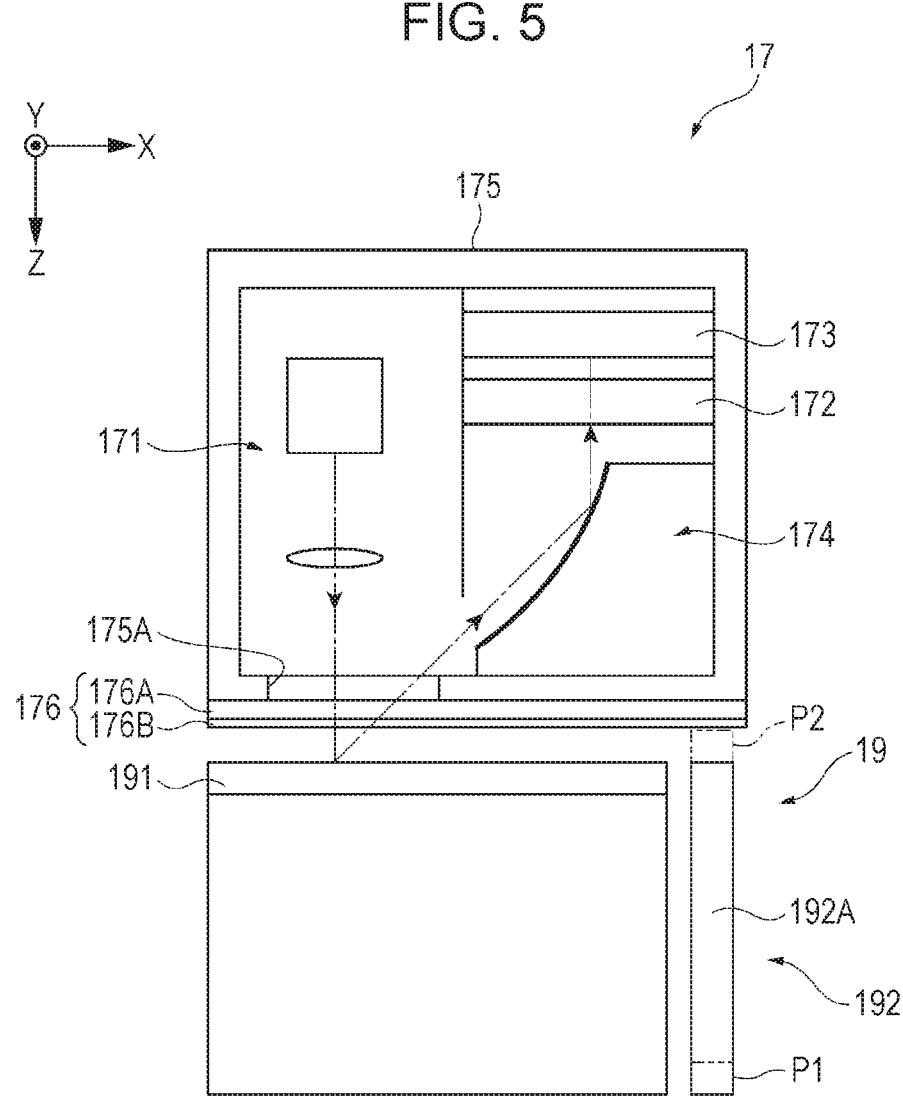
FIG. 5 is a schematic diagram illustrating the schematic configuration of the adjustment unit of the first embodiment.

FIG. 5 is a schematic diagram illustrating the schematic configuration of the spectrometer 17 and the adjustment unit 19.

The adjustment unit 19 is used for performing various adjustments to enable the spectrometer 17 to carry out the spectral measurement appropriately, and is configured to include the white reference plate 191 and the cleaning mechanism 192.

The white reference plate 191 corresponds to a reference object of the disclosure, and has known spectral characteristics (reflectance). The white reference plate 191 is used as a spectral measurement target when carrying out white correction or acquiring reference light, and, as illustrated in FIG. 1, is disposed on the −X side of the platen 122.

The cleaning mechanism 192 subjects the window section 176 of the spectrometer 17 to cleaning and removes the dirtiness, such as ink, which is adhered to the window section 176. As illustrated in FIG. 1, the cleaning mechanism 192 is disposed between the platen 122 and the white reference plate 191 in the X direction on the outside (the −X side) of the transport path of the medium A when viewed from the Z direction. The cleaning mechanism 192 is configured to include an abutting member 192A which abuts the window section 176 of the spectrometer 17, and a drive mechanism (not shown) which moves the abutting member 192A forward and backward along the Z direction.

The abutting member 192A is formed of a resin material having flexibility and elasticity, for example, and is used for wiping dirtiness, such as ink, which is adhered to the surface of the window section 176 and removing the dirtiness. When not carrying out the cleaning, the abutting member 192A is disposed at a standby position P1 (illustrated with a solid line in FIG. 5) distanced from the window section 176 of the spectrometer 17, and when carrying out the cleaning, the abutting member 192A is disposed in an abutting position P2 (illustrated with a double-dot-dash line in FIG. 5) at which it is possible to abut the window section 176 of the spectrometer 17.

The cleaning operation of the window section 176 by the cleaning mechanism 192 will be described later in detail.

Configuration of Control Unit

As illustrated in FIG. 2, the control unit 15 is configured to include an I/F 151, a unit control circuit 152, a memory 153, and a central processing unit (CPU) 154.

The I/F 151 inputs the print data which is input thereto from the external device 20 to the CPU 154.

The unit control circuit 152 is provided with a control circuit which controls each of the supply unit 11, the transport unit 12, the printing section 16, the light source 171A, the variable wavelength interference filter 5, the light receiving section 173, and the carriage movement unit 14. The unit control circuit 152 controls the operations of each unit based on command signals from the CPU 154. Note that, the control circuit of each unit may be provided separately from the control unit 15 and be connected to the control unit 15.

The memory 153 stores various programs and various data which control the operations of the printer 10.

Examples of the various data include: V-λ data indicating the wavelength of light which is transmitted by the variable wavelength interference filter 5 in relation to the voltage applied to the electrostatic actuator 56 when controlling the variable wavelength interference filter 5; print program file data which stores each ink ejection amount in relation to the color data included as print data; and the like.

Note that the memory 153 may also store the light emission properties (the emission spectrum) of the light source 171A in relation to each wavelength, the light receiving properties (the reception photo-sensitivity properties) of the light receiving section 173 in relation to each wavelength, and the like.

Figure 6:
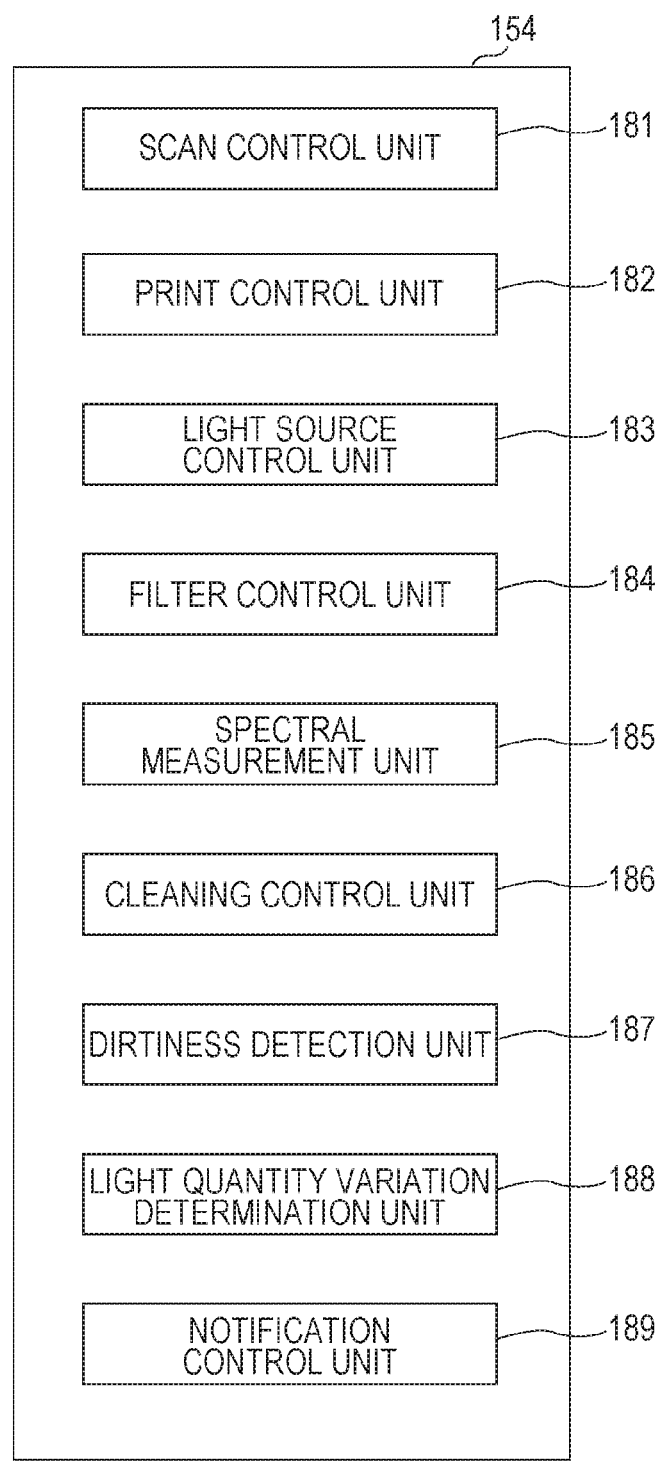
FIG. 6 is a block diagram illustrating the configuration of each function of a control unit in the first embodiment.

FIG. 6 is a block diagram illustrating the functional configuration of the CPU 154 of the control unit 15 of the printer 10.

As illustrated in FIG. 6, by reading and executing various programs stored in the memory 153, the CPU 154 functions as a scan control unit 181, a print control unit 182, a light source control unit 183, a filter control unit 184, a spectral measurement unit 185, a cleaning control unit 186, a dirtiness detection unit 187, a light quantity variation determination unit 188, and a notification control unit 189.

The scan control unit 181 outputs a command signal to the unit control circuit 152 instructing the driving of the supply unit 11, the transport unit 12, and the carriage movement unit 14. Accordingly, the unit control circuit 152 supplies the medium A to the transport unit 12 by driving the roll drive motor of the supply unit 11. The unit control circuit 152 drives the transport motor of the transport unit 12 to transport a predetermined region of the medium A along the Y direction to a position at which the region faces the carriage 13 of the platen 122. The unit control circuit 152 drives the carriage motor 142 of the carriage movement unit 14 to move the carriage 13 along the X direction.

The print control unit 182 outputs a command signal to the unit control circuit 152 instructing the control of the printing section 16 based on the print data. Note that, the print data may be stored in the memory 153, and may be input from the external device 20.

When the command signal is output from the print control unit 182 to the unit control circuit 152, the unit control circuit 152 outputs a print control signal to the printing section 16, and ejects ink onto the medium A by driving the piezo elements provided in the nozzles such that the dot occupation rate of each color in each pixel becomes a value corresponding to the print control signal. Note that, when carrying out the printing, a dot forming operation in which the carriage 13 moves along the X direction and dots are formed by causing the ink to be ejected from the printing section 16 during the movement, and a transport operation in which the medium A is transported in the Y direction are repeated alternately, and an image formed of a plurality of dots is printed onto the medium A.

The light source control unit 183 carries out lighting control of the light source section 171. For example, the light source control unit 183 causes the light source section 171 to emit light under drive conditions (a drive current value and a drive voltage value) at which the emitted light quantity reaches a predetermined value according to the light emitting characteristics of the light source section 171, which are stored in the memory 153. As described later, when variation in the light quantity is detected by the light quantity variation determination unit 188, the light source control unit 183 adjusts the light quantity if it is possible to adjust the light quantity of the light source section 171.

The filter control unit 184 reads a drive voltage to the electrostatic actuator 56 corresponding to the wavelength of light that the variable wavelength interference filter 5 is to be allowed to transmit from the V-λ data of the memory 153 and outputs a command signal to the unit control circuit 152. Accordingly, the unit control circuit 152 applies the drive voltage, as a command, to the variable wavelength interference filter 5 and light of a predetermined transmission wavelength is transmitted by the variable wavelength interference filter 5.

The spectral measurement unit 185 may be provided as a spectral measurement section, and measures the light quantity of the light transmitted by the variable wavelength interference filter 5 based on the detection signal outputted by the light receiving section 173. The spectral measurement unit 185 performs the color measurement of the measurement target using the acquired measured value.

The cleaning control unit 186 corresponds to a cleaning control section, and carries out the cleaning of the window section 176 (i.e., a cleaning process) by controlling the cleaning mechanism 192 when dirt (e.g., a residue) is detected on the window section 176 by the dirtiness detection unit 187. The dirtiness detection unit 187 may detect dirt when the light quantity variation determination unit 188 detects a reduction in the light quantity of the light source section 171. Note that, the cleaning process may be carried out according to the instructions or the like of a user, and may be carried out at a predetermined timing which is set in advance.

The dirtiness detection unit 187 corresponds to a dirtiness detecting section, and detects ink residue on the window section 176 based on the correlation between the reference value and the measured value of the light quantity of each measurement wavelength. For example, the reference value may be the initial value when a product is delivered from a factory and is the light quantity of each measurement wavelength which is a spectral measurement result of the white reference plate 191. The measured value of the light quantity of each measurement wavelength is the spectral measurement result of the white reference plate 191 which is measured by the spectral measurement unit 185 (a dirtiness detection process). The dirtiness detection process will be described in detail later.

The light quantity variation determination unit 188 corresponds to a light quantity variation determination section, and determines whether or not the light quantity of the light source section 171 has changed based on the reference value in relation to the white reference plate 191 and the measured value which is the spectral measurement result by the spectral measurement unit 185 (a light quantity variation determination process). The light quantity variation determination unit 188 carries out regression analysis using each measured value of the white reference plate 191, which is measured by the spectral measurement unit 185 before and after the cleaning process is carried out, and the reference value. The light quantity variation determination unit 188 determines whether or not there is light quantity variation of the light source section 171 based on the slope of the regression line. In the present embodiment, when the light quantity variation determination unit 188 detects that there is a likelihood that the light quantity has decreased, the light quantity variation determination unit 188 discerns whether or not the decrease is by the influence of a reduction in the light quantity of the light source section 171 by carrying out the cleaning and removing the influence of ink on the window section 176. This light quantity variation determination process will be described in detail later.

When a variation in the light quantity of the light source section 171 is detected by the light quantity variation determination unit 188 and it is detected that it is not possible to adjust the light quantity of the light source section 171 by the light source control unit 183, the notification control unit 189 carries out a notification process in which the user is notified of the variation in the light source light quantity. Accordingly, it is possible to urge the user to exchange the light source.

Note that, the control unit 15 is also configured to be capable of realizing various functions such as a calibration function in which the print profile data is corrected (updated), as appropriate, using the color measurement results of a correction test pattern, a white reference, or the like.

Detailed description will be given later of the operations of the functional configuration of the control unit 15.

Adjustment Process of Printer

Next, the adjustment process (including processes relating to the dirtiness detection method of the disclosure) by the printer 10 will be described based on the drawings as an example of a driving method of the printer 10 of the present embodiment.

Figure 7:
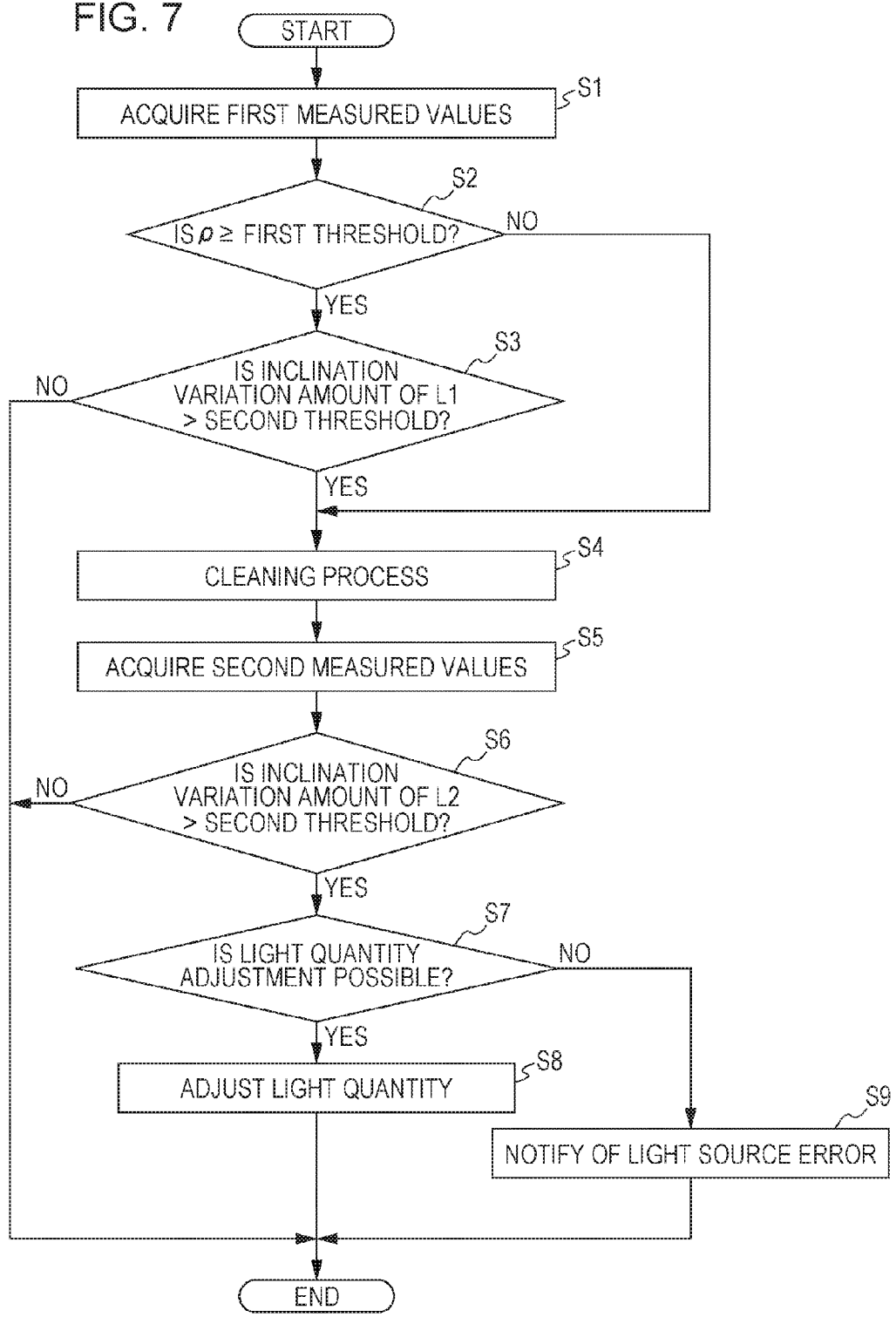
FIG. 7 is a flowchart illustrating an adjustment process in the printer of the first embodiment.

FIG. 7 is a flowchart illustrating an adjustment process in the printer 10.

In the adjustment process illustrated in FIG. 7, the dirtiness of the window section 176 is detected based on the first measured values obtained by carrying out the spectral measurement of the white reference plate 191 (the dirtiness detection process), and the cleaning of the window section 176 is carried out. In the adjustment process described above, it is determined whether or not the light quantity of the light source section 171 has changed (the light quantity variation determination process), and a process is carried out according to the determination results.

Note that, for example, the printer 10 may carry out the adjustment process at a predetermined timing, such as when the white correction is carried out, and may carry out the adjustment process according to the instructions of the user.

In the present embodiment, the wavelength region, which is the measurement target, is a visible light region, for example, from 400 nm to 700 nm. The spectral measurement is carried out based on the light quantities of the light of 16 measurement wavelengths with a 20 nm interval, using 700 nm as the initial wavelength.

Dirtiness Detection Process

When the adjustment process is carried out, the printer 10 first carries out the dirtiness detection process of detecting the dirtiness of the window section.

In the dirtiness detection process, first, the spectral measurement is carried out on the white reference plate 191, the light quantities of the light of the 16 measurement wavelengths are measured, and the first measured values are acquired (step S1).

In step S1, the spectrometer 17 is moved to a position facing the white reference plate 191 by the scan control unit 181. The control unit 15 carries out the spectral measurement on the surface of the white reference plate 191. In other words, the light source control unit 183 lights the light source 171A and sequentially changes the drive voltage applied to the electrostatic actuator 56 of the variable wavelength interference filter 5 using the filter control unit 184. The spectral measurement unit 185 acquires the output values of 16 bands which are at a 20 nm interval from the initial wavelength as the first measured values.

Next, the dirtiness detection unit 187 determines whether or not a correlation coefficient ρ is greater than or equal to a first threshold (step S2). The correlation coefficient ρ is based on the correlation between the first measured values and the reference values of the output values of the 16 bands in relation to the white reference plate 191. The reference values may be, for example, initial values or designed values which are measured values when a product is delivered from a factory or the like.

Here, when the correlation coefficient ρ is less than the first threshold, ink or the like may be adhering to the window section 176, and it is determined that the window section 176 is dirty. Therefore, when it is determined that the correlation coefficient ρ is less than the first threshold (no in step S2), the dirtiness detection unit 187 causes the cleaning control unit 186 to carry out the cleaning process in order to subject the window section 176 to cleaning (step S4). The cleaning process will be described later.

Hereinafter, description will be given of a method of detecting dirtiness of the window section 176 according to the correlation coefficient ρ.

Figure 8:
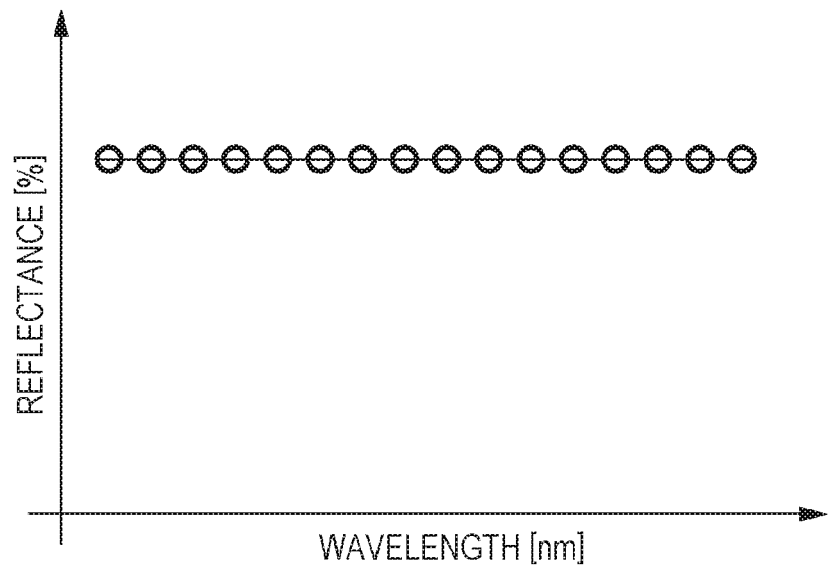
FIG. 8 is a diagram illustrating an example of reference values of reflectance in the first embodiment.
Figure 9:
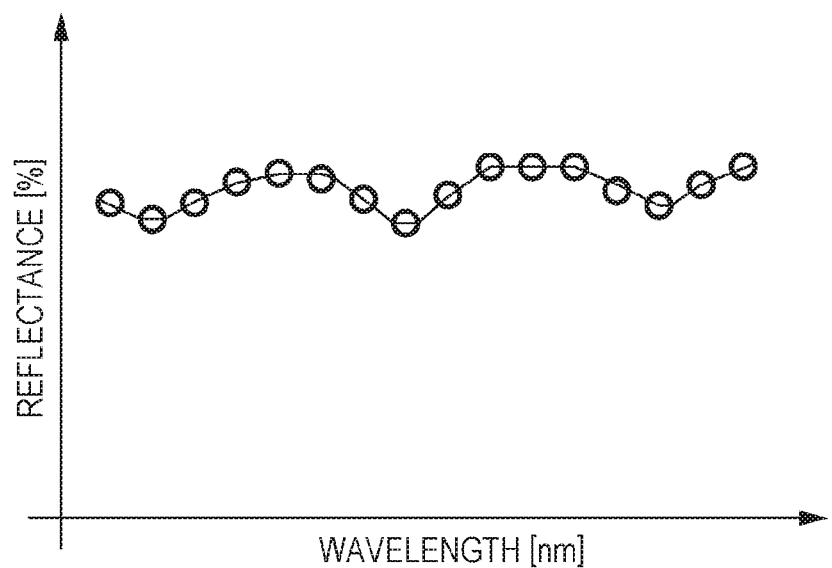
FIG. 9 is a diagram illustrating an example of measured values of the reflectance in the first embodiment.

FIG. 8 is a diagram schematically illustrating the reflectance (the reference values) of the white reference plate 191 when the window section 176 is not dirty with ink. FIG. 9 is a diagram schematically illustrating the reflectance (the reference values) of the white reference plate 191 when there is an ink residue.

When the window section 176 is not dirty with ink, the white reference plate 191 has a reflectance of approximately 100% as illustrated in FIG. 8, and when there is an ink residue, there are wavelengths at which the reflectance decreases, as illustrated in FIG. 9. This is because, due to a portion of the transmitted light of wavelengths corresponding to a type (color) of ink which is adhered to the window section 176 being absorbed, the measured values of the received light quantity in the wavelengths are reduced. Note that, the measured values of the received light quantity are acquired as voltage values corresponding to the received light receiving section in the light receiving section 173, for example.

Figure 10:
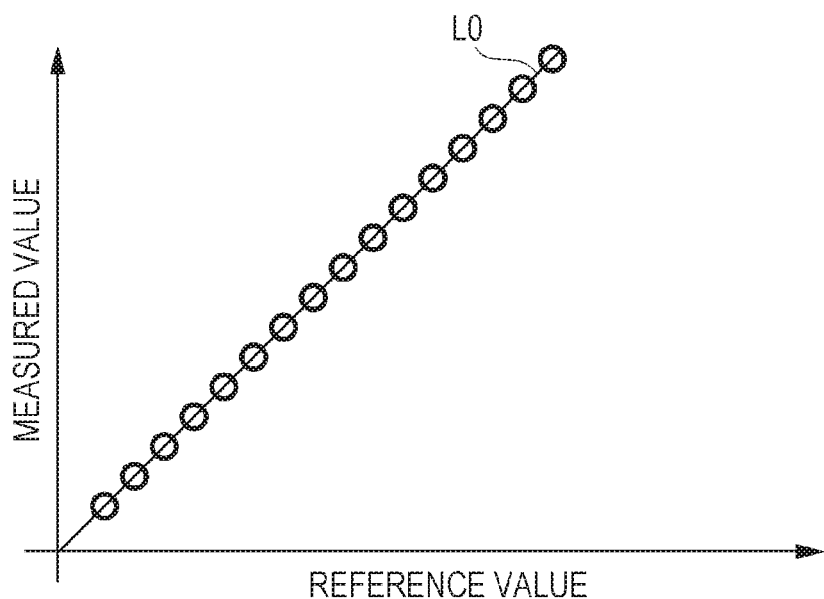
FIG. 10 is a diagram illustrating an example of the correlation between reference values and first measured values when a window section is not dirty.
Figure 11:
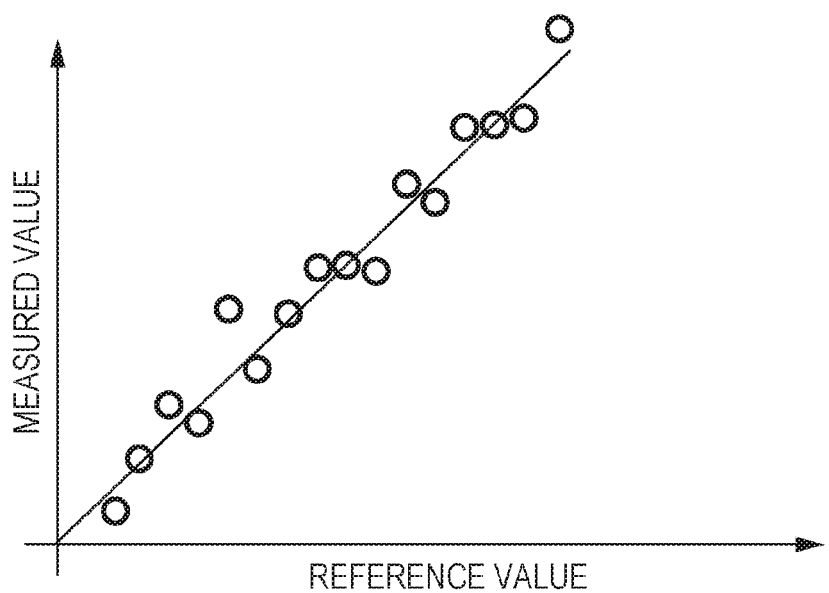
FIG. 11 is a diagram illustrating an example of the correlation between reference values and first measured values when a window section is dirty.

FIG. 10 is a diagram of the correlation between the reference values and the first measured values when the first measured values substantially match the reference values. FIG. 11 is a diagram of the correlation between the reference values and the first measured values when the window section 176 is dirtied with ink. Note that, in FIGS. 10 and 11, the predictor variable (the horizontal axis) is set as the reference value, and the criterion variable (the vertical axis) is set as the measured value (for example, a voltage value).

Note that, the reference values are reference values of measured values (for example, voltage values) obtained by measuring the white reference plate 191 at each of the 16 bands, are measured when a product is delivered from a factory or the like, and stored in the memory 153.

As illustrated in FIG. 10, when the reference values and the first measured values substantially match, each point corresponding to each of the 16 bands is positioned on a straight line (a reference line L0) of a slope 1.

Meanwhile, as illustrated in FIG. 11, when the window section 176 is dirty with ink or stated in another way, has an ink residue, each point corresponding to each of the 16 bands is not disposed on the straight line (a first regression line described later), and there is variation in the positions. Ordinarily, when there is an ink residue, the magnitude (the absolute value) of the correlation coefficient ρ indicating the correlation between the first measured values and the reference values decreases since there is a bias in the adherence amount of ink adhered to the window section 176 for each color.

Note that, the correlation coefficient ρ can be acquired as a value obtained by dividing the average of the deviation products of the measured values and the reference values by a standard deviation of the measured values and a standard deviation of the reference. Since the correlation coefficient ρ in the present embodiment is a positive value, the absolute value of the correlation coefficient will be referred to simply as the correlation coefficient.

Here, for example, the first threshold is set according to the color measurement performance of the spectrometer 17 or the spectral measurement unit 185, and when the correlation coefficient ρ is greater than or equal to the first threshold, the first measured values are set so as to be values corresponding to a range of the repeatability of the white corresponding to the color measurement performance.

As described above, since the correlation coefficient ρ decreases when there is an ink residue, it is possible to detect the dirtiness of the window section by detecting that the correlation coefficient ρ is less than the first threshold using the dirtiness detection unit 187.

Light Quantity Variation Determination Process

In the printer 10, continuing from the dirtiness detection process described above, the light quantity variation determination process of detecting the variation in the light quantity of the light source section 171 is carried out. Note that, in the present embodiment, description is given of an example in which the light quantity of the light source section 171 is reduced.

Returning to FIG. 7, in step S2, when it is determined that the correlation coefficient ρ is greater than or equal to the first threshold (yes in step S2), that is, when no variation in the correlation coefficient ρ caused by dirt (e.g., ink residue) on the window section 176 is detected, the light quantity variation determination unit 188 determines the variation amount of the slope of a first regression line L1 (step S3). The first regression line L1 is acquired using regression analysis based on the first measured values and the reference values exceed a second threshold in relation to the reference slope 1 of the reference line L0 (refer to FIG. 12).

Figure 12:
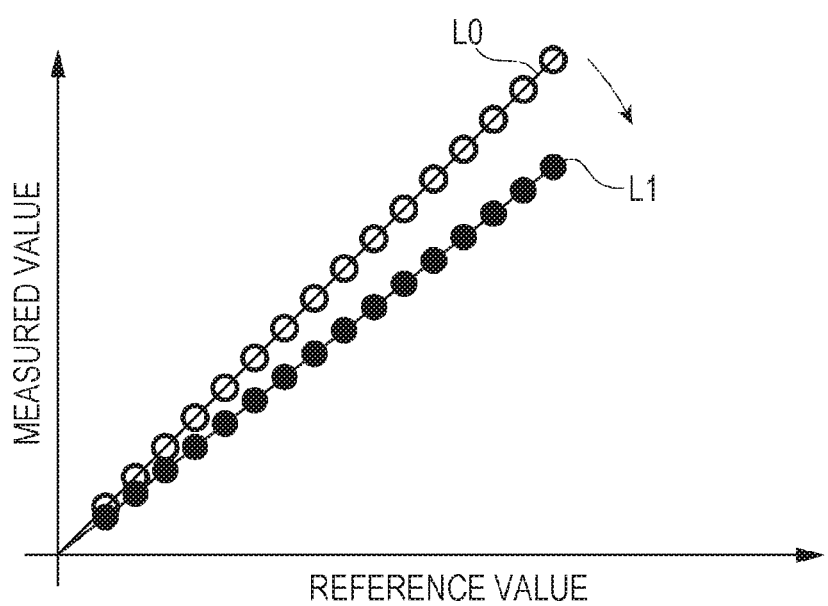
FIG. 12 is a diagram illustrating an example of the correlation between reference values and first measured values in the first embodiment.

FIG. 12 is a diagram of the correlation between the first measured values and the reference values. In FIG. 12, an example of a correlation diagram when the first measured values match the reference values is indicated using white-filled circles, and an example of a correlation diagram when the light quantity of the light source section 171 is reduced in relation to the reference values is indicated using black circles. Note that, in the examples illustrated in FIG. 12, the window section 176 is not dirty with ink.

As illustrated in FIG. 12, when the first measured values match the reference values, each point corresponding to each of the 16 bands is positioned on the reference line LO which is the straight line of the slope 1, as described above. Meanwhile, when the light quantity of the light source section 171 is reduced, since the values of the first measured values are reduced, the slope of the first regression line L1 decreases, as illustrated in FIG. 12. Therefore, it is possible to detect the variation in light quantity based on the variation in the slope of the first regression line L1. Note that, it is possible to calculate the first regression line L1 using the least-squares method or the like.

In the present embodiment, the second threshold is set in advance based on the allowable variation amount of the light quantity values which is set according to the color measurement precision. Therefore, when the slope of the first regression line L1 varies in excess of the second threshold in relation to the slope of the reference line L0, this indicates that the slope of the first regression line L1 falls outside of the predetermined allowable range. In other words, the light quantity values vary in excess of the allowable variation amount, and thus, it is possible to determine that there is a likelihood of an abnormality (reduction) in the light quantity of the light source section 171.

Returning to FIG. 7, when the variation of the slope of the first regression line L1 is within the second threshold in relation to the slope of the reference line L0 (no in step S3), there is no variation in the light quantity of the light source section 171, it is determined that the window section 176 is not dirty, and the processes of the present flowchart are ended.

Meanwhile, when the variation of the slope of the first regression line L1 exceeds the second threshold in relation to the slope of the reference line L0 (yes in step S3), the light quantity variation determination unit 188 causes the cleaning control unit 186 to carry out the cleaning process (step S4). In other words, even when there is no abnormality in the light quantity of the lighting light from the light source section 171, a case is considered in which the variation in the slope of the first regression line L1 is greater than or equal to the second threshold due to the measured values being uniformly reduced in relation to each wavelength due to the dirtiness of the window section 176. Therefore, in the present embodiment, as described later, after carrying out the cleaning process of the window section 176, the variation of the light quantity of the light source section 171 is determined again. In the cleaning process, the cleaning process of the window section 176 is performed by the cleaning mechanism 192 to remove, for example, ink. The cleaning process will be described later in detail.

Once the cleaning process is completed, the light quantity variation determination unit 188 causes the spectral measurement of the white reference plate 191 to be carried out in the same procedure as in step S1, and acquires second measured values (step S5).

Next, in the same manner as in step S3, the light quantity variation determination unit 188 determines whether or not the variation amount of the slope of a second regression line L2 which is acquired through regression analysis based on the second measured values and the reference values exceeds the second threshold in relation to the reference slope (the slope of the reference line L0) (step S6).

When the variation amount of the slope of the second regression line L2 is within the second threshold in relation to the slope of the reference line L0 (no in step S6), no variation is detected in the light quantity of the light source section 171. Since the slope of the second regression line L2 is restored to 1, which is the reference slope, the light quantity variation determination unit 188 ends the process of the present flowchart.

In other words, by referencing the slope of the second regression line L2, it can be understood that the received light quantity of the light receiving section 173 is restored to a value substantially the same as the reference value during the acquisition of the second measured value. The reason that the received light quantity is restored is because the light quantity value of the light source section 171 did not vary in excess of the allowable amount in relation to the reference value, and any dirt (e.g., ink) on the window section 176 which had reduced the received light quantity corresponding to the measured value is removed by the cleaning process.

When the variation amount of the slope of the second regression line L2 in relation to the slope of the reference line L0 exceeds the second threshold (yes in step S6), the light quantity variation determination unit 188 determines the variation in the light quantity of the light source section 171. In other words, due to the received light quantity not being restored even if the cleaning process is carried out, it can be understood that the reduction in the slope of the second regression line L2 is caused by a variation in the light quantity of the light source section 171.

When a variation in the light quantity of the light source section 171 is detected, the light source control unit 183 determines whether or not it is possible to adjust the light quantity of the light source section 171 (step S7). When it is determined that it is possible to adjust (increase) the light quantity of the light source section 171 by adjusting the drive current value (the voltage value) (yes in step S7), the light source control unit 183 carries out the light quantity adjustment (step S8) and ends the process of the present flowchart. The adjustment of the light quantity may be performed by adjusting the drive current value (the voltage value) such that the light quantity value becomes the same as the reference value (the initial value) based on the light emission characteristics of the light source section 171 which are stored in advance, for example.

Note that, in order to determine whether or not the light quantity of the light source section 171 has reached the predetermined value, the spectral measurement of the white reference plate 191 may be carried out again.

Meanwhile, when it is determined that it is not possible to adjust the light quantity of the light source section 171 by adjusting the drive current value (the voltage value) (no in step S7), the notification control unit 189 carries out an error notification process of notifying the user of a light source error (step S9) and ends the process of the present flowchart. Although not depicted in the drawings, the error notification process causes a display device or the like provided in the external device 20 to display a notification screen for indicating that the light quantity is varied in excess of an adjustable range. Not limited to an image, the notification may be performed by causing an audio output device to output audio. An information output device, such as a display device or an audio output device, may be provided in the printer 10.

Cleaning Process

Figure 13:
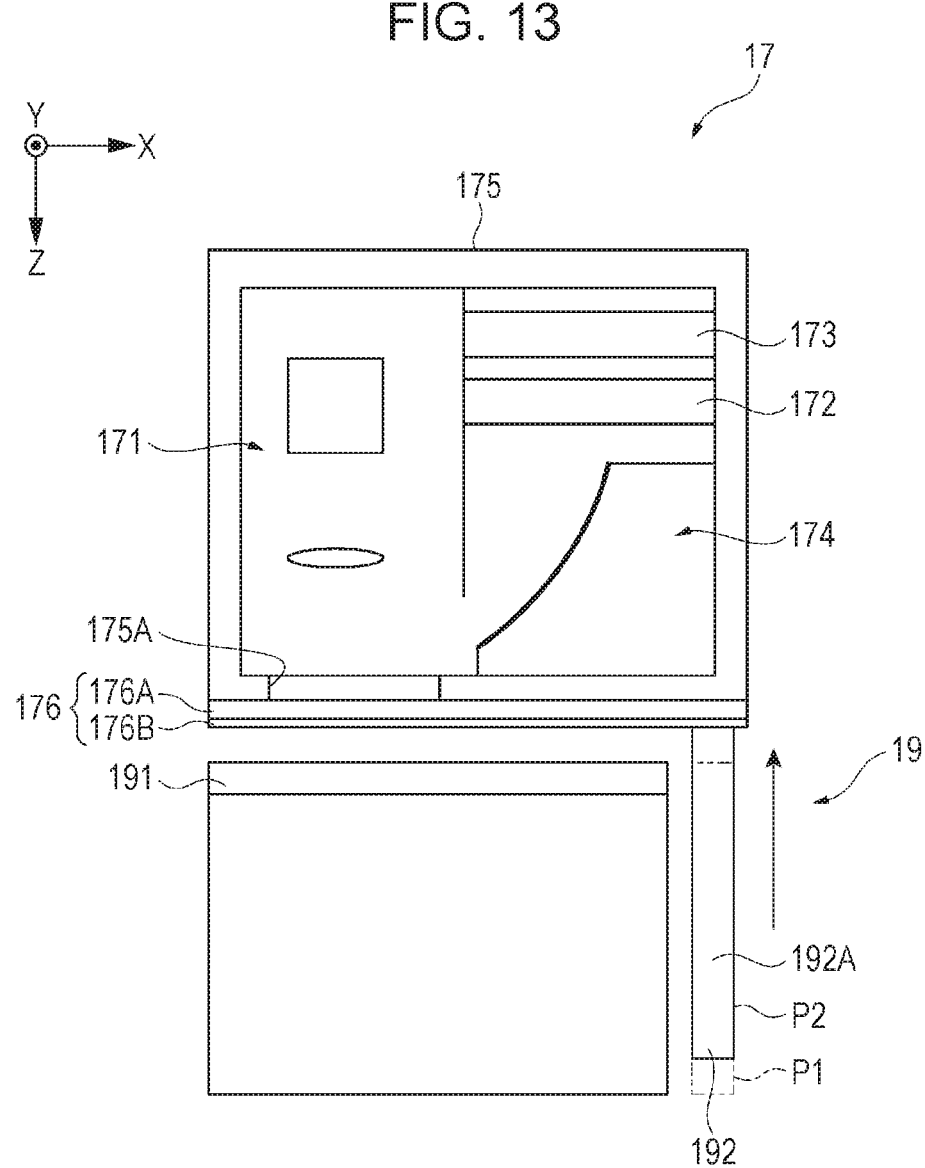
FIG. 13 is a schematic diagram illustrating an example of a procedure of cleaning in the first embodiment.

FIGS. 13 and 14 are schematic diagrams illustrating an example of a procedure of cleaning of the window section 176 by the cleaning mechanism 192.

When the cleaning process of the window section 176 is carried out (step S4 illustrated in FIG. 7), the cleaning control unit 186 first moves the abutting member 192A which is disposed at the standby position P1 illustrated in FIG. 5 to the abutting position P2 illustrated in FIG. 13.

The cleaning control unit 186 moves the carriage 13 along the X direction once the abutting member 192A is moved to the abutting position P2. In other words, the scan control unit 181 moves the carriage 13, that is, the spectrometer 17, along the X direction based on the drive conditions (the drive timing, movement amount, and the like) set by the cleaning control unit 186. Dirt that adheres to the window section 176 is wiped by the abutting member 192A and is removed due to the spectrometer 17 being moved in a state in which the abutting member 192A is abutting the window section 176.

Once the scan control unit 181 causes the carriage 13 to move a predetermined amount, the scan control unit 181 causes the carriage 13 to stop. The cleaning control unit 186 moves the abutting member 192A to the standby position P1 and ends the cleaning process.

Note that, in the depicted example, the cleaning is performed while moving the carriage 13 which is disposed in a position facing the white reference plate 191 in the +X direction; however, the carriage 13 may be moved in the −X direction. The carriage 13 may be reciprocally moved in the X directions, and the total movement amount in the cleaning process is not particularly limited.

Operation Effects of First Embodiment

In the present embodiment, the first measured values are obtained by carrying out the spectral measurement of the white reference plate 191, and the dirtiness of the window section 176 is detected based on the reference values and the first measured values.

Here, there is a case in which an ink mist is generated by the ejection of the ink from the printing section 16, and the ink mist adheres to the window section 176 of the spectrometer 17. When the ink mist adheres to the window section 176, the light of a specific wavelength corresponding to the color of the adhered ink is absorbed when the light from the white reference plate 191 is transmitted by the window section 176. Therefore, the measured value corresponding to the light quantity of the specific wavelength is reduced. Note that, as in the present embodiment, in a configuration in which the spectrometer 17 is embedded in the carriage 13 integrally with the printing section 16, the ink mist adheres more easily to the spectrometer 17 than in the case in which the spectrometer 17 and the printing section 16 are separate.

To handle this, it is possible to detect dirt (e.g., ink) on the window section 176 by detecting the variation in the first measured values caused by the ink residue based on the reference values and the first measured values, and it is possible to detect a reduction in the color measurement precision caused by the ink residue on the window section 176.

As described above, since light of a specific wavelength corresponding to the color of the ink adhered on the window section 176 is absorbed, the measured value corresponding to the light of the specific wavelength decreases, and the value of the correlation coefficient ρ also decreases. Accordingly, it is possible to detect the dirtiness of the window section 176 based on the correlation coefficient ρ between the reference values and the first measured values. For example, by determining whether or not the correlation coefficient ρ is greater than or equal to the first threshold, it is possible to more reliably detect a reduction in the color measurement precision that is caused by the ink residue on the window section 176.

The light quantity variation determination unit 188 determines the variation in the light quantity of the light source section 171 based on the slope of the regression line. The measured values are values corresponding to the light quantity received by the light receiving section 173, and the measured values vary according to the light quantity of the light source section 171. Therefore, when there is no variation in the slope of the regression line, it is possible to determine that there is no variation in the light quantity of the light source section 171, and when there is variation in the slope, it is possible to determine that there is a likelihood that there is variation in the light quantity of the light source section 171. In this manner, in the present embodiment, it is possible to determine whether or not there is variation in the light quantity of the light source section 171 by referring to the slope of the regression line.

The light quantity variation determination unit 188 determines whether or not the variation amount of the slope of the regression line exceeds the second threshold. In other words, whether or not the slope of the regression line falls within the allowable range when determining the light quantity variation. When the light quantity is reduced due to degradation or the like of the light source section 171, ordinarily, the greater the light quantity of a wavelength, the greater the variation amount of the light quantity, and the smaller the light quantity of a wavelength, the smaller the variation amount of the light quantity. Therefore, when the first measured values (the light quantity values) are reduced in relation to the reference values, the slope of the regression line decreases accordingly in relation to 1. Since the variation in the slope of the regression line corresponds to the variation in the light quantity of the light source section 171, it is possible to determine whether or not the light quantity of the light source section 171 varies in excess of the allowable range based on whether or not the slope of the regression line falls within the allowable range.

The light quantity variation determination unit 188 carries out the cleaning when the variation amount of the slope of the first regression line L1, which is acquired before carrying out the cleaning in relation to the reference slope, exceeds the second threshold. When the variation amount of the slope of the second regression line L2, which is acquired after carrying out the cleaning in relation to the reference slope, exceeds a predetermined threshold, the variation in the light quantity of the light source section 171 is determined.

Here, the measured values correspond to received light quantities of the light receiving section 173 and change according to variation in the light quantity of the light source section 171, a reduction in the light quantity of a specific wavelength caused by ink residue on the window section 176, and the like. Therefore, other than being caused by a variation in the light quantity of the light source section 171, there is a likelihood that the variation in the slope of the first regression line L1 may be caused by a reduction in the received light quantity caused by ink residue on the window section 176 as described above.

In the present embodiment, by referring to the slope of the first regression line L1, it is possible to detect that there is a likelihood that the light quantity of the light source section 171 changed, and it is possible to carry out the cleaning. By referring to the slope of the second regression line L2 after carrying out the cleaning, it is possible to suppress the influence of a reduction in the received light quantity caused by dirtiness of the window section 176, and it is possible to more reliably determine the variation in the light quantity of the light source section 171.

In the present embodiment, when dirt or in other words, an ink residue, is detected on the window section 176 as described above, the cleaning is carried out using the cleaning mechanism 192. Accordingly, it is possible to remove the ink which is adhered to the window section 176, and it is possible to suppress a reduction in the color measurement precision caused by the adherence of the ink.

The cleaning mechanism 192 positions the abutting member 192A in the abutting position P2 during cleaning and positions the abutting member 192A in the standby position P1 at times other than during the cleaning. Accordingly, it is possible to suppress wear (degradation) of the abutting member 192A caused by the abutting member 192A abutting the window section 176 at times other than during the cleaning. It is also possible to suppress the degradation of the hydrophobic film 176B which is formed on the surface of the window section 176.

The window section 176, which is the cleaning target of the cleaning mechanism 192, is configured by forming the hydrophobic film 176B on the surface of the light transmissive member 176A, which covers the opening portion 175A.

Accordingly, it is possible to easily remove the ink even when the ink is adhered to the window section 176.

In the present embodiment, the variable wavelength interference filter 5, which is a Fabry-Pérot etalon, is used as a dispersing element. Accordingly, by sequentially changing the dimensions of the gap G between the pair of reflecting films 54 and 55, it is possible to extract light of a plurality of wavelengths in a short time, and it is possible to obtain a shortening of the time necessary for measurement. By using the Fabry-Pérot etalon, which has a small size, it is possible to obtain a reduction in the size of the image forming apparatus in comparison to a case in which an acousto-optic tunable filter (AOTF), a liquid crystal tunable filter (LCTF), or the like is used.

Second Embodiment

Next, description will be given of the second embodiment according to the disclosure. Note that, in the following description, aspects of the configuration and processes, which are the same as those of the first embodiment, will be assigned the same reference symbols, and description thereof will be omitted or simplified.

In the first embodiment described above, a configuration is exemplified in which the dirtiness detection unit 187 detects the dirtiness of the window section 176 based on the correlation coefficient ρ, which is calculated using the first measured values. In contrast, the second embodiment differs from the first embodiment in that the spectral measurement unit 185 calculates a color difference ΔE between the first measured values and the reference values, and the dirtiness detection unit 187 detects the dirtiness of the window section 176 based on the color differences.

FIG. 15 is a flowchart illustrating an adjustment process in the printer 10.

In the dirtiness detection process of the adjustment process of the present embodiment, first, in the same manner as in the first embodiment, the spectral measurement is carried out on the white reference plate 191, the light quantities of the light of each of the 16 measurement wavelengths are measured, and the first measured values are acquired (step S1).

Next, the dirtiness detection unit 187 determines whether or not the color difference ΔE exceeds a third threshold (step S11).

In the present embodiment, the dirtiness detection unit 187 calculates the color difference ΔE using the first measured values and the reference values. Note that, it is possible to calculate the color difference ΔE based on various systems such as $\Delta E_{ab}$, $\Delta E_{94}$, $\Delta E_{00}$, and the like.

Here, for example, the third threshold is set according to the color measurement performance of the spectrometer 17 or the spectral measurement unit 185, and when the color difference ΔE is less than or equal to the third threshold, the first measured values are set so as to be values corresponding to a range of the repeatability of the white corresponding to the color measurement performance.

As described above, since the value of the color difference ΔE, which is calculated based on the first measured values and the reference values, increases when there is ink on the window section 176, it is possible to detect the ink residue (i.e., dirt) by determining that the color difference ΔE exceeds a first predetermined value using the dirtiness detection unit 187.

Note that, when it is determined that the color difference ΔE is less than or equal to the third threshold (yes in step S11), it is determined that the color difference ΔE falls within the allowable range and that the window section 176 is not dirty, and the light quantity variation determination process is carried out in the same manner as in the first embodiment.

When it is determined that the color difference ΔE exceeds the third threshold (no in step S11), the dirtiness detection unit 187 causes the cleaning control unit 186 to carry out the cleaning process (step S4). Subsequently, the light quantity variation determination process is carried out in the same manner as in the first embodiment.

Operation Effects of Second Embodiment

In the present embodiment, the dirtiness of the window section 176 is detected based on the color difference ΔE, which is calculated using the reference values and the measured values.

Here, when ink adheres to the window section 176, as described above, since the light of a specific wavelength corresponding to the color of the ink is absorbed, the color difference ΔE increases. Therefore, by referring to the color difference ΔE, it is possible to detect a change in the color based on the reference values and the measured values. Therefore, it is possible to determine that there might be ink on the window section 176, and it is possible to detect a reduction in the color measurement precision caused the adherence of the ink.

MODIFICATION EXAMPLE

Note that, the disclosure is not limited to the embodiments described above, and configurations obtained by modification, improvement, combination, as appropriate, of the embodiments, and the like within a range in which it is possible to achieve an aspect of the disclosure are included in the disclosure.

In the embodiments described above, the measured values of the white reference plate 191 when a product is delivered from a factory or the like are used as the reference values, using the white reference plate 191 having known spectral characteristics as a reference object during the acquisition of the reference values and the measured values by carrying out the spectral measurement; however, the disclosure is not limited thereto. For example, a white paper surface of the medium A may be used as the reference object. A color patch or the like of a known color may be used as the reference object.

In the embodiments described above, a configuration is exemplified in which a reference object of a known color is used; however, the disclosure is not limited thereto. For example, measured values obtained by using the spectrometer 17 may be used as the new reference values. For example, the measured values of a case in which no abnormalities are detected after carrying out the adjustment process may be set as the new reference values.

In the embodiments described above, a case is exemplified in which the light quantity values are used as the reference values and the measured values; however, the disclosure is not limited thereto. In other words, the reflectance, the chromaticity, or the like, which are calculated from the light quantity values, may be used as the reference values and the measured values. Note that, different types of value may be used for the reference values and the measured values.

In the second embodiment, a configuration is exemplified in which the color difference is acquired based on the measured values and the reference values, and the ink on the window section 176 is detected by detecting the color variation based on the color difference; however, the disclosure is not limited thereto. In other words, other than the color difference, the variation in the chromaticity (variation in the hue or the chroma) or the like may be calculated as the evaluation values with which to quantitatively evaluate the color variation using the reference values and the measured values.

In the embodiments described above, a configuration is exemplified in which the light quantity variation determination process is carried out after carrying out the dirtiness detection process; however, the disclosure is not limited thereto. In other words, when dirt (e.g., ink residue) is detected by the dirtiness detection process, and when dirt is not detected after carrying out the cleaning process, the process may end.

In the embodiments described above, a configuration is exemplified in which, after dirtiness of the window section 176 is detected by the dirtiness detection process, the cleaning process is carried out, and a light quantity decrease determination process is carried out; however, the disclosure is not limited thereto. For example, a configuration may be adopted in which, in the dirtiness detection process, when dirtiness is detected in a dirtiness detection step (step S2 in FIG. 7 and step S11 in FIG. 15), after carrying out the cleaning process, the process returns once more to a measuring step of acquiring the first measured values, and the dirtiness detection step is carried out using the re-acquired measured values. Accordingly, it is possible to determine whether or not the ink is removed in the cleaning process.

The dirtiness detection process described above may be carried out repeatedly. In this case, when it is determined that there is a likelihood that ink remains even if the cleaning process is performed a predetermined number of times, there is a likelihood that the ink may not be removed even if the cleaning process is carried out, and there is a likelihood that the reference object has changed color or is dirty. There is also a likelihood that the light emission spectrum of the light source section 171 has changed. Therefore, in this case, an abnormality in that may not be possible to handle using the cleaning process or by adjusting the light quantity of the light source may be detected, and notification of the detection results may be performed.

In the embodiments described above, after acquiring the second measured values (step S5), the determination of whether or not the variation amount of the slope of the second regression line L2 exceeds the second threshold (step S6) is carried out; however, the disclosure is not limited thereto.

For example, after acquiring the second measured values, the determination of whether or not the correlation coefficient ρ based on the second measured values is greater than or equal to the first threshold and the determination of whether or not the color difference ΔE is less than or equal to the third threshold may be carried out. In other words, the dirtiness detection step may also be carried out. In the cleaning process of step S4, only a portion of the ink residue which reduced the light quantity is removed, and there is a likelihood that another portion is not removed. In this case, the value of the correlation coefficient ρ is reduced (the color difference ΔE increases). Therefore, by carrying out the above-described determination based on the acquired second measured values, it is possible to determine whether or not the ink residue is completely removed.

When it is determined that the ink residue is not removed, each of the processes of the cleaning process, the acquisition of the second measured values, and the dirtiness detection based on the second measured values may be performed a predetermined number of times. When the correlation coefficient ρ is less than the first threshold, even if the processes are carried out the predetermined number of times, it is considered that the removal of the ink may be impossible, or, the light emission spectrum of the light source section 171 has changed. Therefore, even in this case, an abnormality in that may not be possible to handle using the cleaning process or by adjusting the light quantity of the light source may be detected, and notification of the detection results may be performed.

In the embodiments described above, a halogen lamp, a xenon lamp, a white LED, or the like are exemplified as the light source 171A; however, the disclosure is not limited thereto. For example, white light may be emitted using LEDs of each color of RGB.

Here, in a configuration in which a plurality of colors of light source are lit at the same time, the regression line may be separated into the wavelength regions of each light source. From a regression line based on the reference values and the measured values when only R is lit, a regression line when only G is lit, and a regression line when only B is lit, abnormalities in the light quantity of each light source may be determined.

When a plurality of light sources are lit at the same time, the reference values for each light source may be acquired, only one may be lit, and abnormalities in the light quantity of the light source of each light source may be determined individually.

In the embodiments described above, a configuration provided with the cleaning mechanism 192 is exemplified; however, a configuration not provided with the cleaning mechanism 192 may be adopted. In this case, when the dirtiness of the window section 176 is detected, a notification process is performed to provide a notification that it is necessary to perform the cleaning, and the cleaning may be carried out by a user.

In the embodiments described above, the hydrophobic film 176B is formed on the surface of the window section 176; however, the disclosure is not limited thereto, and the hydrophobic film 176B may not be formed.

FIGS. 16A and 16B are schematic diagrams illustrating another example of the cleaning process of the disclosure.

In the embodiments described above, a configuration in which the cleaning mechanism 192 only cleans the spectrometer 17 is exemplified; however, the disclosure is not limited thereto. For example, a configuration may be adopted in which, when carrying out the cleaning of the spectrometer 17, the printing section 16, which is embedded in the carriage 13 so as to be integral with the spectrometer 17, is also cleaned at the same time.

In other words, as illustrated in FIG. 16A, the abutting member 192A is disposed in the abutting position, and the carriage 13 is moved in the −X direction in a state in which the abutting member 192A abuts the spectrometer 17. As illustrated in FIG. 16B, after cleaning the spectrometer 17, the surface of the platen 122 side of the printing section 16, that is, the surface in which the nozzles are formed is also cleaned by the cleaning mechanism 192.

In the embodiments described above, the carriage movement unit 14 which moves the carriage 13 along the X direction is exemplified; however, the disclosure is not limited thereto. For example, a configuration may be adopted in which the carriage 13 is fixed and the medium A is moved relative to the carriage 13. In this case, it is possible to suppress the vibration of the variable wavelength interference filter 5 which accompanies the movement of the carriage 13, and it is possible to stabilize the transmission wavelength of the variable wavelength interference filter 5.

The transport unit 12 which moves the medium A along the Y direction is exemplified; however, the disclosure is not limited thereto. For example, a configuration may be adopted in which the carriage 13 is moved in the Y direction relative to the medium A.

In the embodiments described above, the cleaning is carried out by moving the spectrometer 17 in relation to the cleaning mechanism 192; however, the disclosure is not limited thereto. In other words, the cleaning may be carried out by moving the cleaning mechanism 192 in relation to the spectrometer 17.

The disclosure is not limited to a configuration in which the ink residue is wiped by abutting the abutting member 192A, and a configuration may be adopted in which the ink residue is removed by absorbing the ink, and as long as the configuration is capable of removing the dirtiness of the window section, the configuration is not limited.

In the embodiments described above, a configuration is exemplified in which the unit control circuit 152 is provided in the control unit 15; however, as described above, the control units may be separate from the control unit 15 and provided in each unit. For example, a configuration may be adopted in which a filter control circuit, which controls the variable wavelength interference filter 5, and a light reception control circuit, which controls the light receiving section 173, are provided in the spectrometer 17. A configuration may be adopted in which a microcontroller and a storage memory which stores V-λ data are embedded in the spectrometer 17, and the microcontroller controls the variable wavelength interference filter 5 and the light receiving section 173.

In the embodiments described above, the ink jet type printing section 16, which ejects inks which are supplied from ink tanks by driving piezo elements, is exemplified as the printing section 16; however, the disclosure is not limited thereto. For example, as the printing section 16, a configuration in which bubbles are generated in the ink using a heater to eject the ink, or a configuration in which the ink is ejected by an ultrasonic oscillator may be adopted.

The printing section 16 is not limited to the ink jet type, and, for example, it is possible to apply to printers of any printing system, such as a thermal printer using a heat transfer system, a laser printer, or a dot impact printer.

In the embodiments described above, the light transmission type variable wavelength interference filter 5 which transmits light of a wavelength corresponding to the gap G between the reflecting films 54 and 55 from the incident light is exemplified as the variable wavelength interference filter 5; however, the disclosure is not limited thereto. For example, an optically reflective type of variable wavelength interference filter which reflects light of a wavelength corresponding to the gap G between the reflecting films 54 and 55 may be used.

The optical filter device 172 in which the variable wavelength interference filter 5 is stored in the housing 6 is exemplified; however, a configuration may be adopted in which the variable wavelength interference filter 5 is provided directly in the spectrometer 17.

The specific structure when carrying out the disclosure may be formed by combining, as appropriate, the embodiments and modification examples within a scope in which an aspect of the disclosure can be achieved, and may be changed, as appropriate, to other structures or the like.

The entire disclosure of Japanese Patent Application No. 2015-046370, filed Mar. 9, 2015 is expressly incorporated by reference herein.

What is claimed is:

1. An image forming apparatus, comprising:
   an image forming device that ejects an ink; and
   a spectrometer that disperses incident light, wherein the spectrometer includes:
   a window section that transmits the light,
   a dispersing element that disperses light transmitted by the window section, and
   a light receiving element that receives the light dispersed by the dispersing element and outputs detection signals indicative of measured values of a plurality of wavelengths, and wherein:
   residue on the window section is detected based on the measured values corresponding to each of the plurality of wavelengths obtained by spectrally measuring light from a reference object, and reference values corresponding to each of the plurality of wavelengths.

2. The image forming apparatus according to claim 1, further comprising:
   a spectral measurement unit that acquires the measured values based on the detection signals; and
   a dirtiness detecting unit that detects dirtiness of the window section.

3. The image forming apparatus according to claim 2 wherein:
   the dirtiness detecting unit detects a residue on the window section based on a correlation between the reference values and the measured values.

4. The image forming apparatus according to claim 3 wherein:
   the dirtiness detecting unit detects residue on the window section based on a color variation between the reference values and the measured values.

5. The image forming apparatus according to claim 2, further comprising:
   a cleaning mechanism that cleans the window section; and
   a cleaning control unit that operates the cleaning mechanism to carry out the cleaning of the window section when residue is detected by the dirtiness detecting unit.

6. The image forming apparatus according to claim 5 wherein:
   the cleaning mechanism includes an abutting member that abuts the window section when the cleaning of the window section is carried out and is positioned in a standby position distanced from the window section at times other than when the cleaning is carried out.

7. The image forming apparatus according to claim 5, further comprising:
   a light quantity variation determination unit that determines whether there is variation in a light quantity of a light source based on a slope of a regression line that is based on the reference values and the measured values, wherein:
   the spectrometer includes the light source that irradiates a target with light via the window section, and
   after the cleaning of the window section is carried out, the light quantity variation determination unit determines whether there is variation in the light quantity of the light source based on the slope of the regression line.

8. The image forming apparatus according to claim 1, further comprising:

a light quantity variation determination unit that determines whether there is variation in a light quantity of a light source based on a slope of a regression line, wherein:

the regression line is based on the reference values and the measured values, and the spectrometer includes the light source that irradiates a target with light via the window section.

9. The image forming apparatus according to claim 8 wherein:

the light quantity variation determination unit determines that there is variation in the light quantity of the light source when the slope falls outside of a predetermined allowable range.

10. The image forming apparatus according to claim 1, wherein:

the window section includes a light transmissive member and a hydrophobic film which is formed on a surface of a target side of the light transmissive member.

11. The image forming apparatus according to claim 1, wherein:

the dispersing element is a variable-wavelength type Fabry-Pérot etalon.

12. A dirtiness detection method, comprising:

acquiring measured values corresponding to each of a plurality of wavelengths by spectrally measuring light from a reference object; and detecting residue on a window section based on the measured values and reference values corresponding to each of the plurality of wavelengths, wherein the window section transmits light from the reference object.

13. An image forming apparatus, comprising:

an image forming device that ejects an ink; and a spectrometer that disperses incident light, wherein the spectrometer includes:

a window section that transmits the light, a dispersing element that disperses light transmitted by the window section, and a light receiving element that receives the light dispersed by the dispersing element and outputs detection signals indicative of light amount of a plurality of wavelengths;

a spectral measurement unit that determines measured values for each of the plurality of wavelengths based on the detection signals from the light receiving element; and a dirtiness detecting unit that detects a residue on the window section based on the measured values from the spectral measurement unit and reference values corresponding to each of the plurality of wavelengths.

* * * * *